US010139366B2

(12) United States Patent
Atamanchuk et al.

(10) Patent No.: US 10,139,366 B2
(45) Date of Patent: Nov. 27, 2018

(54) ION MOBILITY SPECTROMETRY (IMS) DEVICE WITH CHARGED MATERIAL TRANSPORTATION CHAMBER

(71) Applicant: Smiths Detection Montreal Inc., Montreal (CA)

(72) Inventors: Bohdan Atamanchuk, Mississauga (CA); Volodimir Bondarenko, Mississauga (CA); Vlad Sergeyev, Toronto (CA); Henryk Zaleski, Scarborough (CA); Daniel Levin, Woodbridge (CA); Mark Piniarski, Mississauga (CA); Igor Kubelik, Mississauga (CA); Qunzhou Bian, Milton (CA); Simon Feldberg, Vaughan (CA); Douglas J. Green, Baldwin, MD (US); Brian Boso, Bel Air, MD (US); Atin J. Patel, Mississauga (CA)

(73) Assignee: SMITHS DETECTION MONTREAL INC., Mississauga (CA)

( * ) Notice: Subject to any disclaimer, the term of this patent is extended or adjusted under 35 U.S.C. 154(b) by 0 days.

(21) Appl. No.: 14/218,109

(22) Filed: Mar. 18, 2014

(65) Prior Publication Data
US 2014/0264021 A1 Sep. 18, 2014

Related U.S. Application Data

(60) Provisional application No. 61/802,928, filed on Mar. 18, 2013, provisional application No. 61/860,773, filed on Jul. 31, 2013.

(51) Int. Cl.
*H01J 49/26* (2006.01)
*H01J 49/06* (2006.01)
(Continued)

(52) U.S. Cl.
CPC ............ *G01N 27/622* (2013.01); *H01C 3/06* (2013.01); *H01J 49/0018* (2013.01);
(Continued)

(58) Field of Classification Search
CPC .... G01N 27/622; H01J 29/92; H01J 49/0018; H01J 49/06; H01J 49/062; H01J 49/061; H01C 3/06; H05K 1/118
(Continued)

(56) References Cited

U.S. PATENT DOCUMENTS 3,192,497 A * 6/1965 Bender ................. C03C 27/042
156/293
4,390,784 A * 6/1983 Browning ............ G01N 27/622
250/286
(Continued)

FOREIGN PATENT DOCUMENTS

CA 2839405 12/2012
CN 101044795 A 9/2007
(Continued)

OTHER PUBLICATIONS

Spiral1. (2007). In R. E. Allen (Ed.), The penguin English Dictionary (3rd ed.). London, UK: Penguin. Retrieved from http://search.credoreference.com/content/entry/penguineng/spiral1/0.*
(Continued)

*Primary Examiner* — Michael Logie
(74) *Attorney, Agent, or Firm* — Kevin E. West; Advent, LLP

(57) ABSTRACT

An ion detection assembly is described that includes a drift chamber, an inlet assembly, and a collector assembly. The drift chamber is formed of substantially non-conductive material and/or semi-conductive material. A patterned resistive trace is deposited on one or more of an interior surface or an exterior surface of the drift chamber. The patterned
(Continued)

resistive trace is configured to connect to a source of electrical energy. The inlet assembly and the collector assembly are in fluid communication with the drift chamber. The inlet assembly includes an inlet for receiving a sample, a reaction region for ionizing the sample, and a gate for controlling entrance of the ionized sample to the drift chamber. The collector assembly includes a collector plate for collecting the ionized sample after the ionized sample passes through the drift chamber.

6 Claims, 24 Drawing Sheets

(51) Int. Cl.
*G01N 27/62* (2006.01)
*H01J 49/00* (2006.01)
*H01C 3/06* (2006.01)
*H05K 1/11* (2006.01)

(52) U.S. Cl.
CPC ............ *H01J 49/06* (2013.01); *H01J 49/062* (2013.01); *H05K 1/118* (2013.01)

(58) Field of Classification Search
USPC ................... 250/281, 282, 287, 286, 396 R
See application file for complete search history.

(56) References Cited

U.S. PATENT DOCUMENTS

| | | | |
|---|---|---|---|
| 4,485,387 A * | 11/1984 | Drumheller ........... | B05C 5/0295 118/401 |
| H000406 H * | 1/1988 | Wohltjen .................. | 436/153 |
| 4,853,589 A * | 8/1989 | Vrijssen .................... | 313/477 R |
| 5,021,654 A | 6/1991 | Campbell et al. | |
| 5,093,036 A * | 3/1992 | Shafe et al. ............... | 252/511 |
| 5,280,175 A | 1/1994 | Karl .......................... | 250/287 |
| 5,489,229 A * | 2/1996 | Muti ........................ | H01J 29/485 445/34 |
| 5,661,300 A * | 8/1997 | Hansen et al. ............ | 250/287 |
| 5,773,925 A * | 6/1998 | Kimura .................... | H01J 9/14 313/412 |
| 5,834,771 A * | 11/1998 | Yoon ........................ | G01N 27/622 250/286 |
| 5,866,194 A * | 2/1999 | Ogawa .................... | B29C 41/085 118/210 |
| 6,040,573 A * | 3/2000 | Sporleder et al. ......... | 250/281 |
| 6,100,521 A * | 8/2000 | Doring et al. ............ | 250/286 |
| 6,369,383 B1 * | 4/2002 | Cornish et al. .......... | 250/286 |
| 6,509,562 B1 * | 1/2003 | Yang ........................ | G01N 27/622 250/287 |
| 6,825,474 B2 * | 11/2004 | Young ...................... | 250/396 R |
| 7,081,618 B2 | 7/2006 | Laprade | |
| 7,155,812 B1 * | 1/2007 | Peterson .................. | H01C 3/06 250/286 |
| 7,224,258 B2 | 5/2007 | Barge et al. | |
| 7,361,206 B1 | 4/2008 | Jahn et al. | |
| 7,498,569 B2 * | 3/2009 | Ding .......................... | 250/282 |
| 7,705,296 B2 | 4/2010 | Wu | |
| 7,714,284 B2 | 5/2010 | Miller et al. | |
| 7,736,592 B2 | 6/2010 | Grande et al. | |
| 8,173,959 B1 | 5/2012 | Boumsellek et al. | |
| 8,258,468 B2 | 9/2012 | Wu | |
| 2002/0113207 A1 * | 8/2002 | Lee et al. ................. | 250/288 |
| 2003/0027022 A1 * | 2/2003 | Arana et al. .............. | 429/17 |
| 2004/0089803 A1 * | 5/2004 | Foley .................... | H01J 49/049 250/288 |
| 2004/0238202 A1 * | 12/2004 | Mathias .................... | 174/100 |
| 2005/0109931 A1 * | 5/2005 | Schultz ............... | G01N 27/622 250/287 |
| 2005/0173629 A1 * | 8/2005 | Miller et al. ............. | 250/290 |
| 2005/0211894 A1 * | 9/2005 | Laprade .................... | 250/287 |
| 2006/0054616 A1 | 3/2006 | Ptasienski et al. | |
| 2007/0262846 A1 | 11/2007 | Barge et al. | |
| 2008/0121797 A1 | 5/2008 | Wu | |
| 2008/0251712 A1 * | 10/2008 | Sanders ................ | H01J 49/004 250/282 |
| 2008/0278278 A1 | 11/2008 | Barge et al. | |
| 2009/0214804 A1 * | 8/2009 | Levine et al. ............. | 428/29 |
| 2010/0209318 A1 | 8/2010 | Grande et al. | |
| 2011/0168882 A1 * | 7/2011 | Hoyes .................... | H01J 49/062 250/283 |
| 2011/0210244 A1 | 9/2011 | Wu | |
| 2011/0277803 A1 * | 11/2011 | Grande et al. ............. | 136/225 |
| 2012/0126109 A1 | 5/2012 | Wu | |
| 2012/0199736 A1 * | 8/2012 | Danel et al. ............. | 250/287 |
| 2013/0009053 A1 * | 1/2013 | Wu ........................ | H01J 49/004 250/282 |
| 2013/0342227 A1 * | 12/2013 | Hozoi et al. ............. | 324/691 |
| 2014/0124663 A1 * | 5/2014 | Green .................. | G01N 27/624 250/290 |
| 2014/0239174 A1 * | 8/2014 | Anderson et al. .......... | 250/288 |
| 2014/0262971 A1 * | 9/2014 | Drumheller ............... | 209/127.1 |
| 2015/0318156 A1 * | 11/2015 | Loyd .................... | H01J 49/068 250/287 |

FOREIGN PATENT DOCUMENTS

| | | | | |
|---|---|---|---|---|
| CN | 101384339 A | | 3/2009 | |
| EP | 2343546 A2 | | 7/2011 | |
| JP | 2002015699 A | * | 1/2002 | ............. H01J 49/06 |
| WO | 20006013396 A2 | | 2/2006 | |
| WO | 2007014303 A2 | | 2/2007 | |
| WO | 2012098364 A1 | | 7/2012 | |
| WO | 2012172436 | | 12/2012 | |

OTHER PUBLICATIONS

Extended European Search Report dated Oct. 4, 2016 for EP Appln. No. 14768277.7.
Office Action dated May 2, 2017 for Chinese Appln. No. 201480028334. 8.
Office Action dated Mar. 28, 2017 for Mexican Appln. No. 25797.
Office Action dated Aug. 24, 2017 for Mexican Appln. No. MX/a/2015/013289.
Office Action dated Nov. 28, 2017 for Japanese Appln. No. 2016-503500.
Office Action dated Feb. 8, 2018 for Russian Appln. No. 2015141390/28.

* cited by examiner

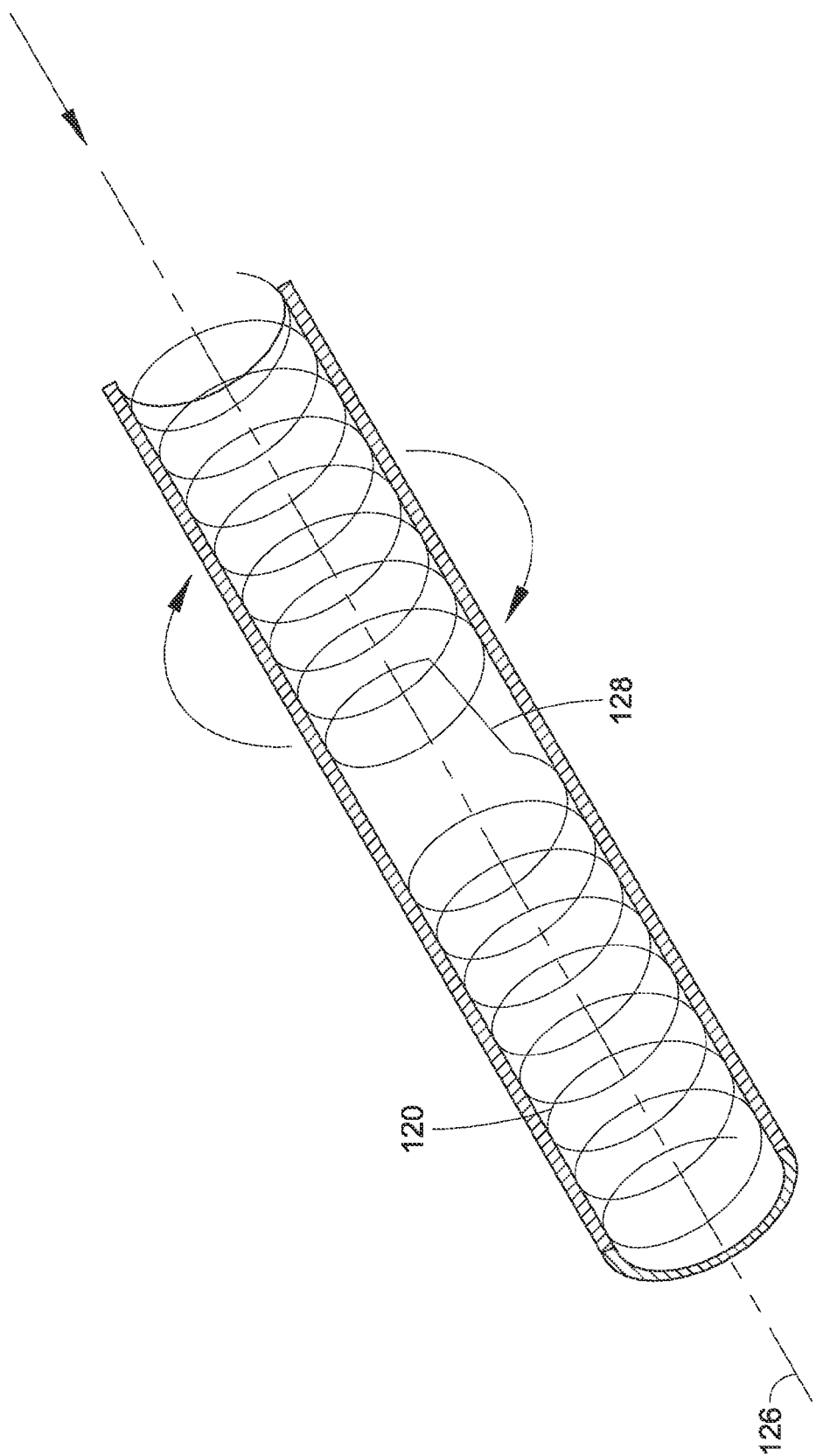

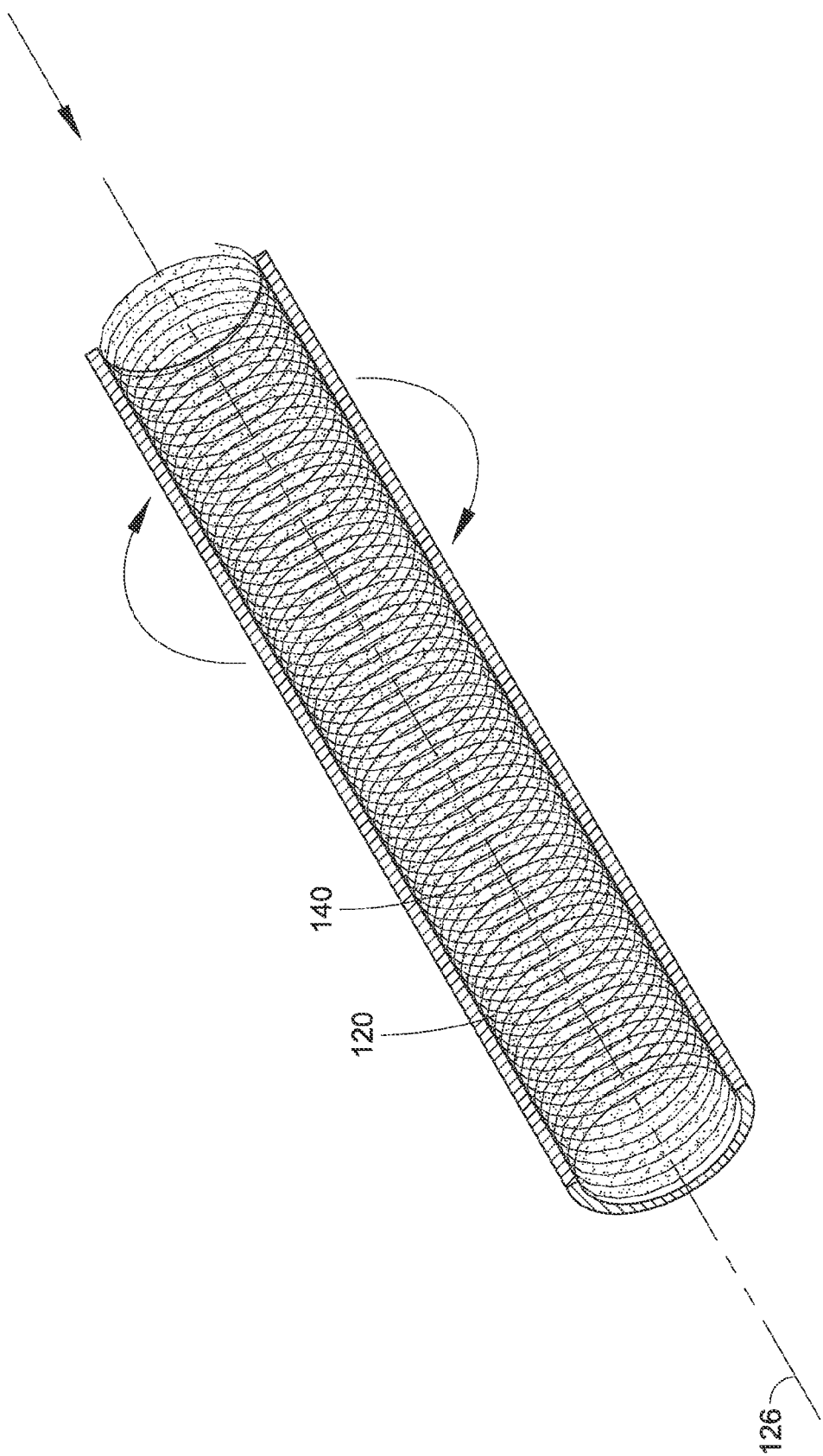

ION MOBILITY SPECTROMETRY (IMS) DEVICE WITH CHARGED MATERIAL TRANSPORTATION CHAMBER

BACKGROUND

Ion mobility spectrometry refers to an analytical technique that can be used to separate and identify ionized material materials, such as molecules and atoms. Ionized material can be identified in the gas phase based on mobility in a carrier buffer gas exposed to an electric field. Thus, an ion mobility spectrometer (IMS) can identify material from a sample of interest by ionizing the material and measuring the time it takes the resulting ions to reach a detector. For example, an IMS detector uses an ion transporting chamber where ionized materials are driven by an electric field from the entrance of the chamber to the exit of the chamber. An ion's time of flight is associated with its ion mobility, which relates to the mass and geometry of the material that was ionized. The output of an IMS detector can be visually represented as a spectrum of peak height versus drift time. In some instances, IMS detection is performed at an elevated temperature (e.g., above one hundred degrees Celsius (+100° C.)). In other instances, IMS detection can be performed without heating. IMS detection can be used for military and security applications, e.g., to detect drugs, explosives, and so forth. IMS detection can also be used in laboratory analytical applications, and with complementary detection techniques such as mass spectrometry, liquid chromatography, and so forth. Multi-section charged material transportation chambers often suffer from limitations, including high cost, complex assembly, frequent and burdensome maintenance, and reliability issues. Other existing single-piece chambers based on a glass or ceramic tube with either a continuous conductive body or an internal continuous conductive coating have non-uniform and/or unstable resistance that can compromise quality of detection.

SUMMARY

An ion detection assembly is described that includes a charged material transportation chamber (e.g., used for ionization/reaction and/or drift regions), an inlet assembly, and a collector assembly. The charged material transportation chamber is formed of substantially non-conductive material and/or semi-conductive material. A patterned resistive trace is deposited on one or more of an interior surface or an exterior surface of the charged material transportation chamber. The patterned resistive trace is configured to connect to a source of electrical energy. The inlet assembly and the collector assembly are in fluid communication with the charged material transportation chamber. The inlet assembly includes an inlet for receiving a sample, a reaction region for ionizing the sample, and a gate for controlling entrance of the ionized sample to the charged material transportation chamber. The collector assembly includes a collector plate for collecting the ionized sample after the ionized sample passes through the charged material transportation chamber.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. The use of the same reference number in different instances in the description and the figures may indicate similar or identical items.

FIG. 14A is a partial cross-sectional isometric view illustrating a charged material transportation chamber with a patterned resistive trace deposited on an interior surface of the charged material transportation chamber, where the substrate is advanced longitudinally at two different rates in accordance with an example implementation of the present disclosure, and where a portion of the substrate is removed to illustrate the pattern of the resistive trace.

FIG. 15A is a partial cross-sectional isometric view illustrating a charged material transportation chamber with a secondary helical resistive trace deposited on an interior surface of the charged material transportation chamber, where the secondary helical resistive trace is deposited over a primary resistive coating in accordance with an example implementation of the present disclosure, and where a portion of the substrate is removed to illustrate the pattern of the resistive trace.

DETAILED DESCRIPTION

Figure 1:
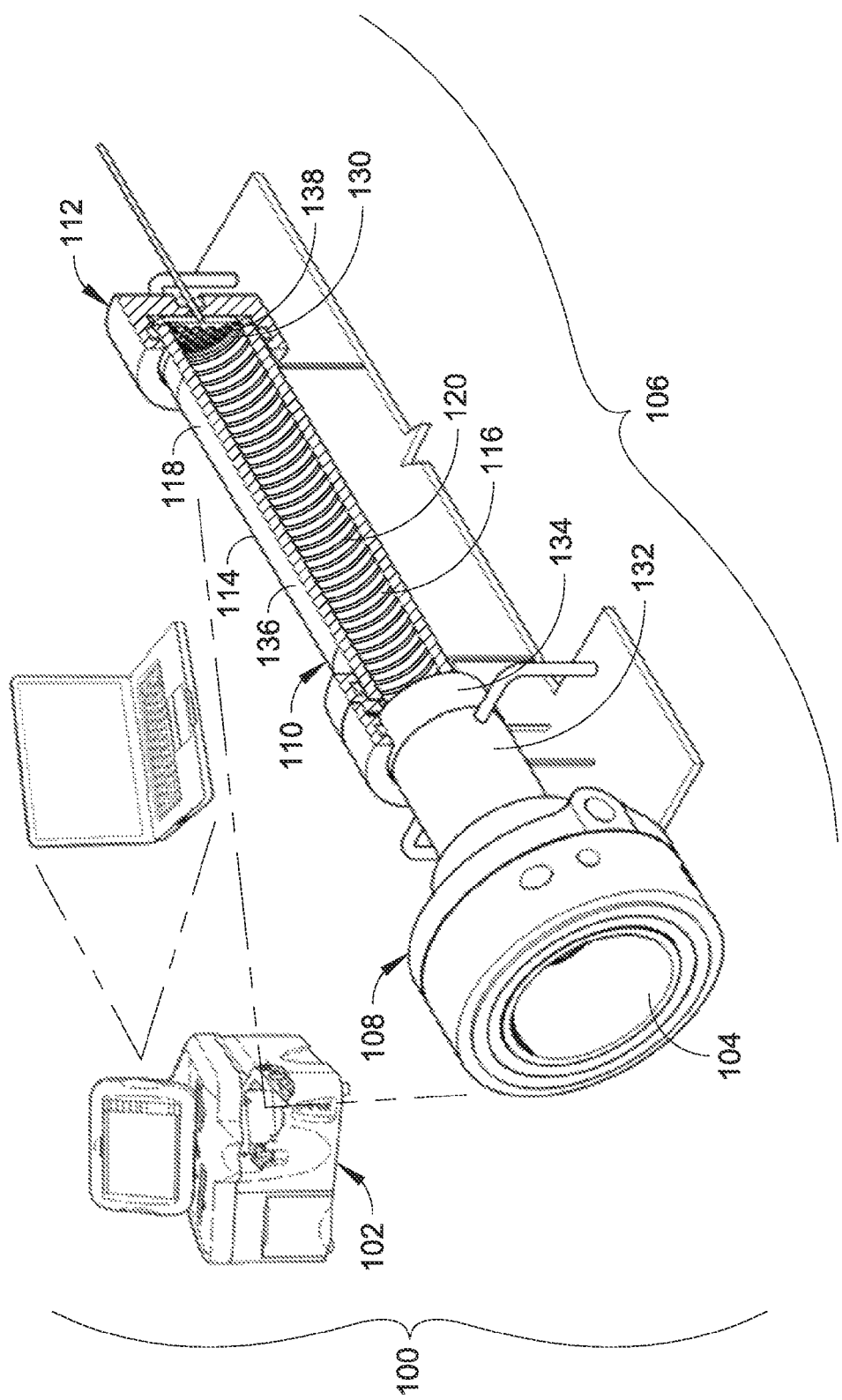
FIG. 1 is a diagrammatic illustration of an IMS system that includes a drift chamber with a patterned resistive trace deposited on an interior surface of the drift chamber in accordance with an example implementation of the present disclosure.

FIG. 1 is an illustration of a spectrometer system, such as an ion mobility spectrometer (IMS) system 100. Although IMS detection techniques are described herein, it should be noted that a variety of different spectrometers can benefit from the structures, techniques, and approaches of the present disclosure. It is the intention of this disclosure to encompass and include such changes. IMS systems 100 can include spectrometry equipment that employs unheated (e.g., surrounding (ambient or room) temperature) detection techniques. For example, an IMS system 100 can be configured as a lightweight explosive detector. However, it should be noted that an explosive detector is provided by way of example only and is not meant to be restrictive of the present disclosure. Thus, techniques of the present disclosure may be used with other spectrometry configurations. For example, an IMS system 100 can be configured as a chemical detector. Further, in other implementations, IMS systems 100 can employ heated detection techniques. For example, an IMS system 100 can be configured as a gently heated detector, a fully heated detector, and so forth. An IMS system 100 can include a detector device, such as a sample detector 102, having a sample receiving port for introducing material (e.g., particles) from a sample of interest to a reaction region/chamber. For example, the sample detector 102 can have an inlet 104 where air to be sampled is admitted to the sample detector 102.

In some implementations, the sample detector 102 can have another device such as a gas chromatograph (not shown) connected in line with the inlet 104. For example, the IMS system 100 can be configured for gas chromatography-ion mobility spectrometry (GC-IMS), where the sample detector 102 is coupled with the gas chromatograph (GC) for common sample introduction (e.g., where a GC capillary column is connected to the sample detector 102 with molecules ionized as they elute from the GC). However, gas chromatography is provided by way of example only and is not meant to be restrictive of the present disclosure. Thus, the sample detector 102 can be used with other detection instrumentation including, but not necessarily limited to: high-pressure liquid chromatography (HPLC), ion mobility spectrometry-mass spectrometry (IMS-MS) (e.g., with quadropole, time-of-flight, and/or Fourier transform cyclotron resonance techniques), liquid chromatography-ion mobility spectrometry-mass spectrometry (LC-IMS-MS), and so forth.

Figure 2:
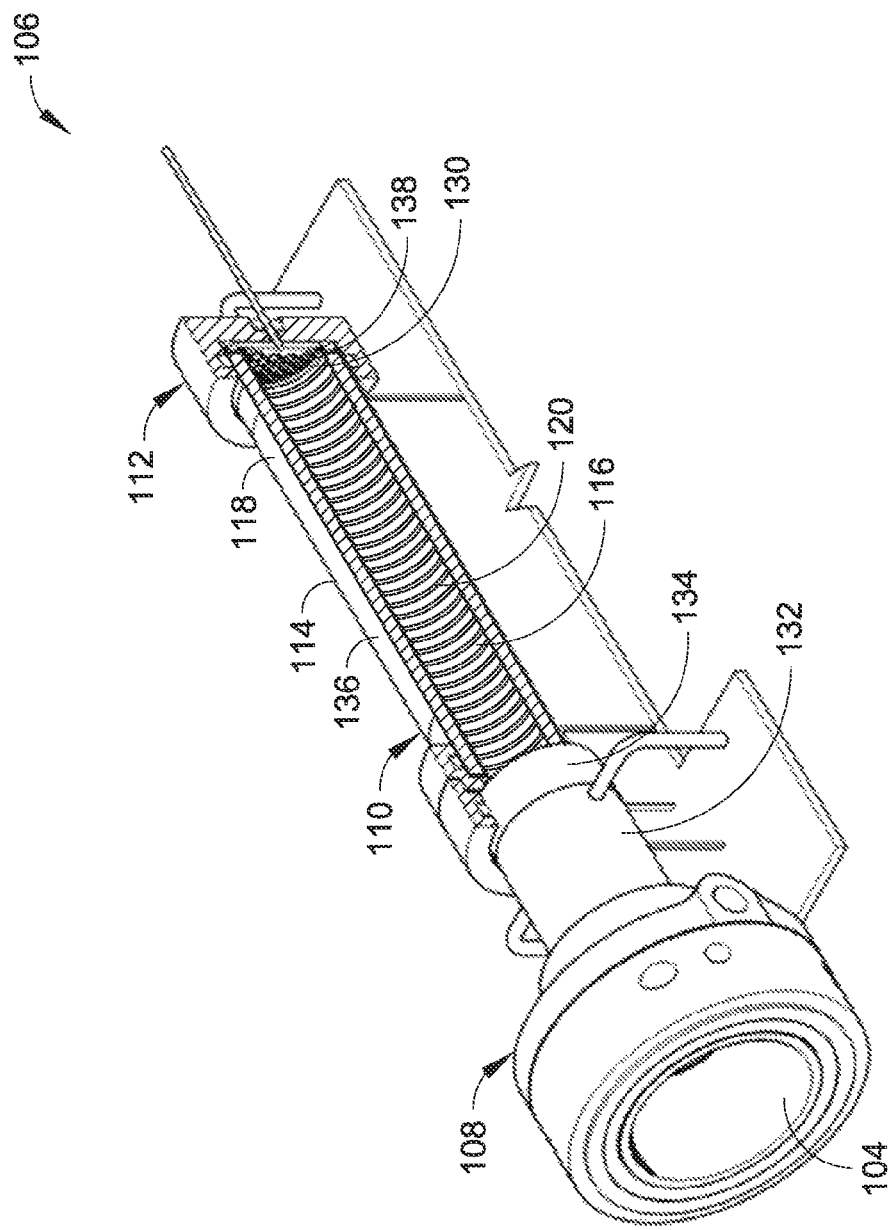
FIG. 2 is a partial cross-sectional isometric view illustrating a drift chamber with a patterned resistive trace deposited on an interior surface of the drift chamber in accordance with an example implementation of the present disclosure.

Referring now to FIG. 2, the inlet 104 is defined by an ion detection assembly 106. The ion detection assembly 106 includes an inlet assembly 108, a reaction/ionization chamber (e.g., a reaction chamber 132), a gate 134, a drift chamber (e.g., a drift tube 110), and a collector assembly 112. The drift tube 110 and/or the reaction chamber 132 comprises a chamber (e.g., a tube 114) having one or more walls formed of substantially non-conductive (e.g., insulating) material including, but not necessarily limited to: a ceramic material (e.g., kaolinite, aluminum oxide, crystalline oxide, a nitride material, a carbide material, silicon carbide, tungsten carbide, and so forth), glass, porcelain, polymer, and/or a composite material. However, these materials are provided by way of example only and are not meant to be restrictive of the present disclosure. Thus, in other implementations, the tube 114 can be constructed using other materials. For example, the tube 114 is constructed of semi-conductive material, which can provide a more uniform electric field within the tube 114 when used with a patterned resistive trace deposited on the inside of the tube 114 (e.g., with respect to a tube constructed of insulating material). In embodiments of the disclosure, one or both of the drift chamber and the reaction/ionization chamber are configured as a charged material transportation chamber including a tube 114 as described herein. For example, in some embodiments, the drift tube 110 includes tube 114. In other embodiments, the reaction chamber 132 includes tube 114. In still further embodiments, the drift tube 110 and the reaction chamber 132 both include a tube 114 (e.g., each including a separate tube 114, both using the same tube 114, each using portions of the same tube 114, and so forth). However, it should be noted that drift chambers and reaction/ionization chambers are provided by way of example only and are not meant to limit the present disclosure. In other embodiments, a charged material transportation chamber including a tube 114 is configured differently.

The tube 114 has an interior surface 116 and an exterior surface 118. Either or both ends of the tube 114 and/or one or more drift segments of the tube 114 are open and allow material (e.g., vapor, particles, and so forth) to pass through the tube 114. A patterned resistive trace 120 is deposited on the interior surface 116 and/or the exterior surface 118 of the tube 114. For example, a resistive trace 120 is printed on the interior surface 116 of the tube 114 and/or the exterior surface 118 of the tube 114 using a conductive ink, a conductive paste, vacuum-deposition, electro-deposition, a chemical treatment, and so forth. In some instances, the drift tube 110 includes more than one patterned resistive trace, such as a first resistive trace 120 printed on the interior surface 116 of the tube 114 and a second resistive trace 120 printed on the exterior surface 118 of the tube 114. A patterned resistive trace provides electrical conductivity along the tube 114, including electrical conductivity at the surface of the tube 114 (e.g., at a patterned resistive trace deposited along the interior surface 116 and/or the exterior surface 118 of the tube 114). Patterned resistive traces can be printed in various regions of an ion detection assembly 106, including, but not necessarily limited to: an inlet region, a reaction region, and so forth.

As described herein, the resistive traces 120 provide a small active internal surface area (e.g., with respect to a typical stackable drift tube). Further, a surface of the tube 114 on which one or more of the resistive traces 120 is disposed is at least substantially free of gaps and/or cavities in which contaminants can accumulate, which could otherwise extend and/or complicate maintenance procedures on the tube 114, such as cleaning cycles and so forth. The resistive traces 120 can provide a continuous, consistent, and/or substantially uniform temperature and/or electric field along the length of the tube 114. In embodiments of the disclosure, geometry of a resistive trace 120 allows for a higher total resistance (e.g., as used in high voltage (HV) power supply implementations) with conductive trace material that has comparatively lower resistivity and can provide better stability of surface resistivity over time. Further, in accordance with the present disclosure, the configurations described herein can reduce and/or minimize electric fields in a direction generally perpendicular to the longitudinal axis of the tube 114, while reducing and/or minimizing penetration of external electrical fields into the interior of the tube 114.

As shown, a drift tube 110 can be of unitary construction, which can provide more reliability than, for example, a typical stackable drift tube configuration. Further, the drift tube 110 does not necessarily require an external housing, thus potentially reducing the costs associated with manufacturing and/or maintenance of, for example, a system 100. In example implementations, a drift tube 110 does not necessarily require an external heating element. For instance, a heating element (e.g., one or more of the resistive traces 120) can be deposited onto the tube 114 (e.g., deposited on the exterior surface 118 of the tube 114) and function to establish a controlled (e.g., heated) temperature for the tube. Such configurations can further reduce the cost and/or complexity of manufacturing a system 100 as described herein. In some embodiments, a resistive trace 120 deposited on the exterior surface 118 of the tube 114 is configured to produce similar electric potential as a resistive trace 120 deposited on the interior surface 116 of the tube 114 (e.g., to provide improved uniformity of the electric field inside the tube 114).

Figure 3:
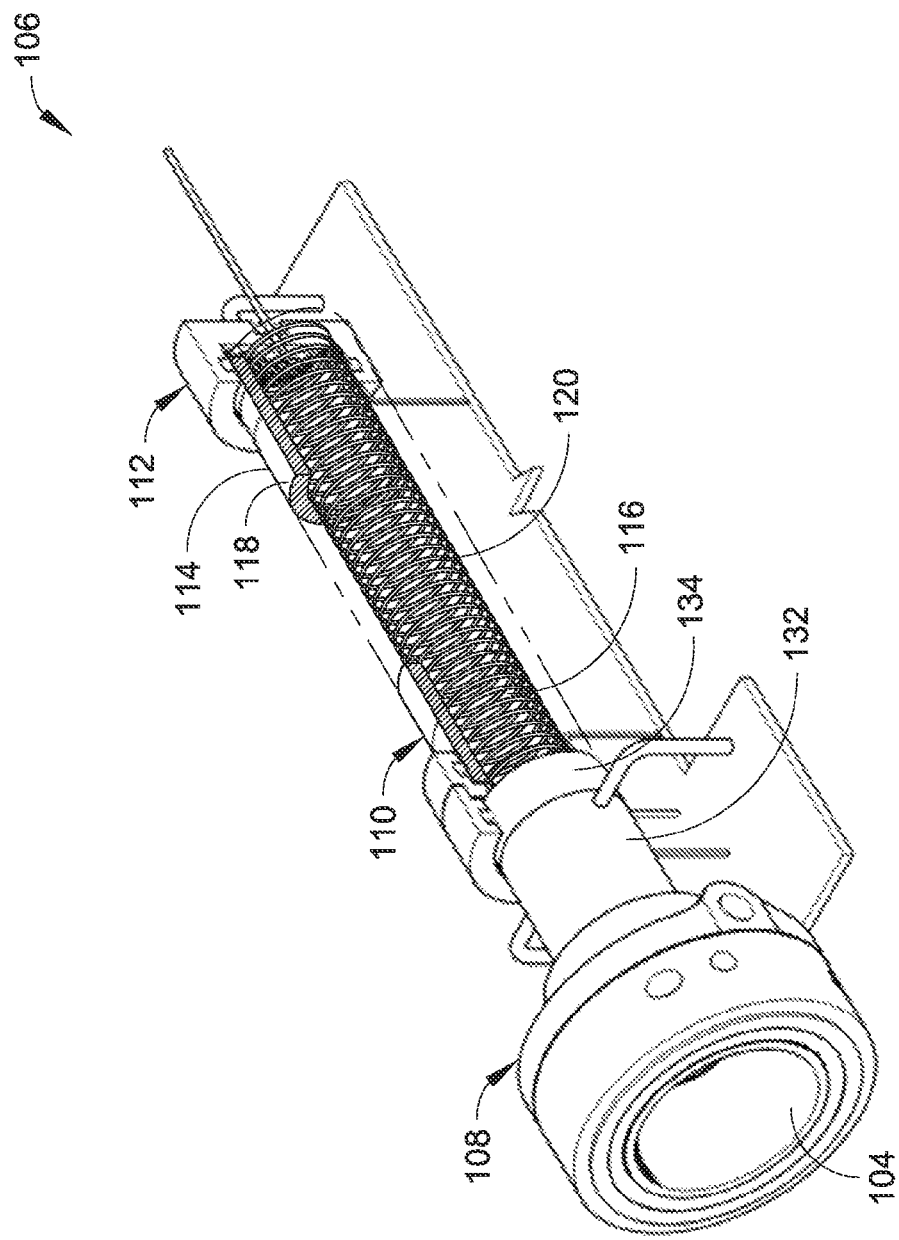
FIG. 3 is a partial cross-sectional isometric view illustrating a drift chamber with a helical resistive trace deposited on an interior surface of the drift chamber in accordance with an example implementation of the present disclosure, where portions of the drift chamber are shown in phantom to illustrate the helical pattern of the resistive trace.
Figure 4:
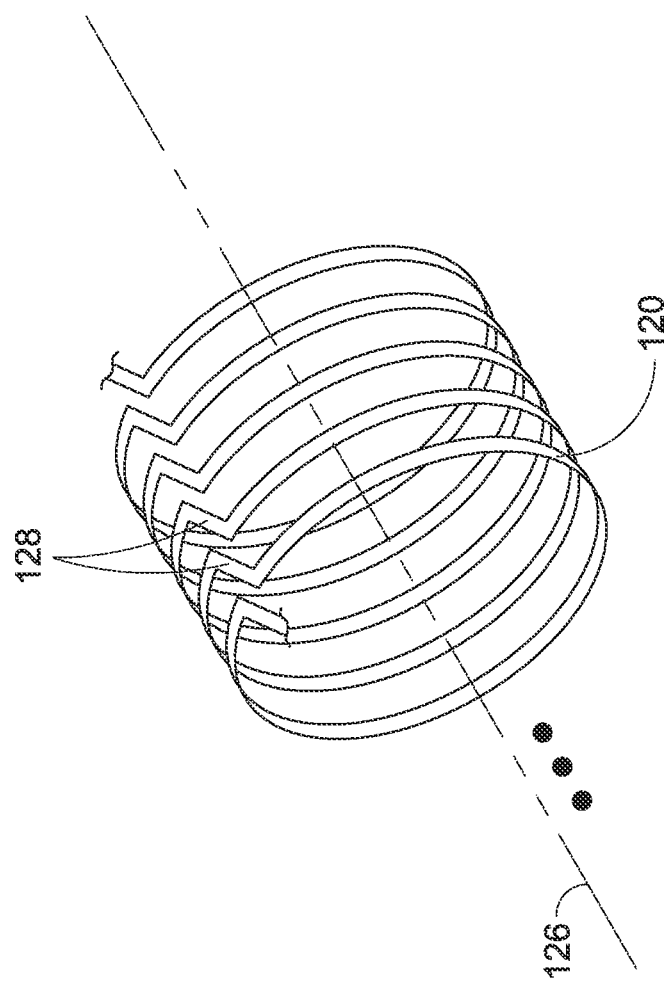
FIG. 4 is a diagrammatic illustration of a pattern for a resistive trace deposited on an interior surface of a charged material transportation chamber, such as the drift chamber illustrated in FIG. 2, where the resistive trace includes multiple turns of more than two hundred and seventy degrees (270°) oriented at least substantially perpendicular to a longitudinal axis of the charged material transportation chamber, and where adjacent turns of the resistive trace are connected to one another in series using jumpers deposited on an interior surface of the charged material transportation chamber in accordance with an example implementation of the present disclosure.
Figure 5:
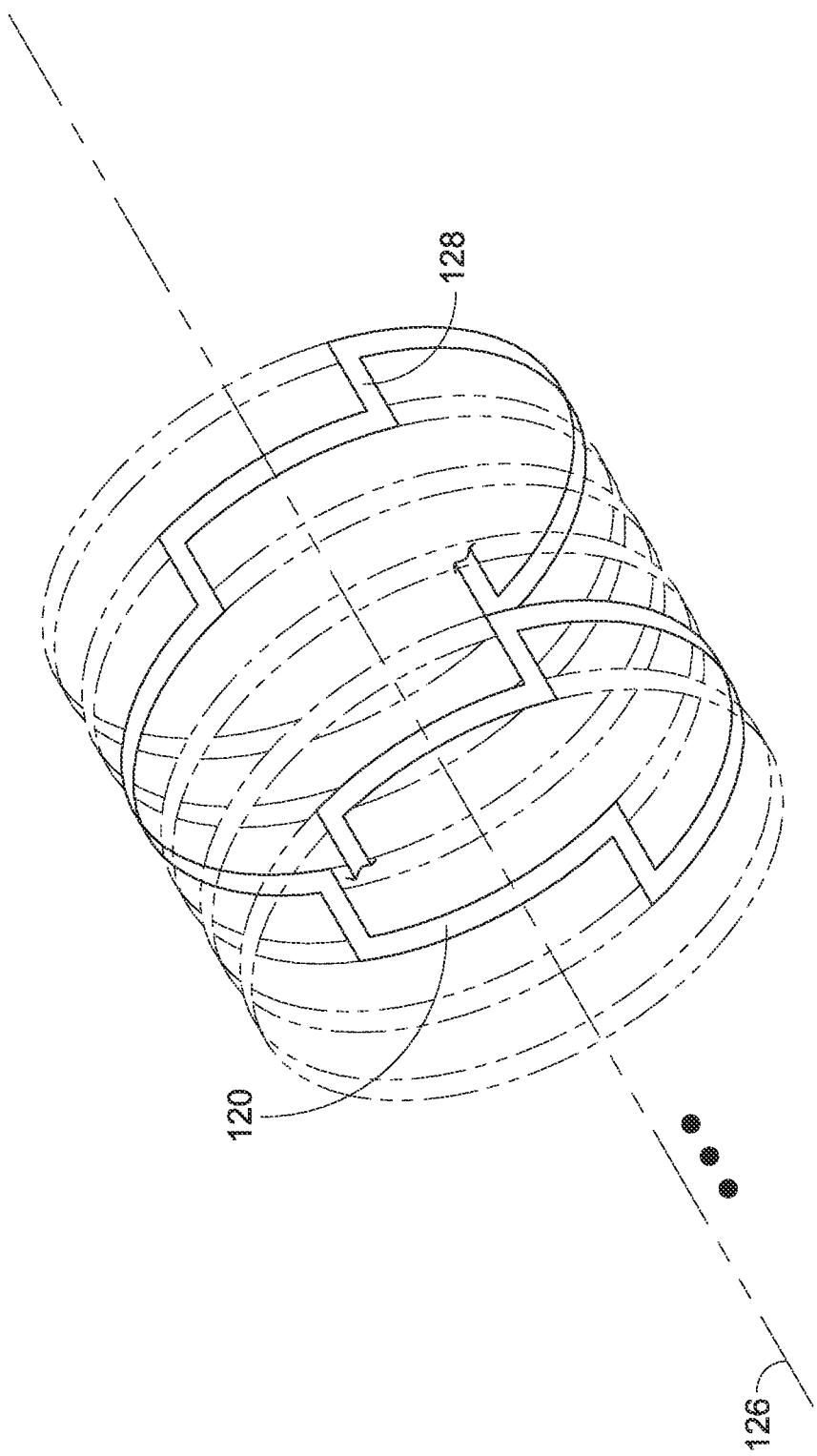
FIG. 5 is a diagrammatic illustration of a pattern for a resistive trace deposited on an interior surface of a charged material transportation chamber, such as the drift chamber illustrated in FIG. 2, where the resistive trace includes multiple turns of less than two hundred and seventy degrees (270°) oriented at least substantially perpendicular to a longitudinal axis of the charged material transportation chamber, and where adjacent turns of the resistive trace are connected to one another in series using jumpers deposited on an interior surface of the charged material transportation chamber in accordance with an example implementation of the present disclosure.
Figure 6:
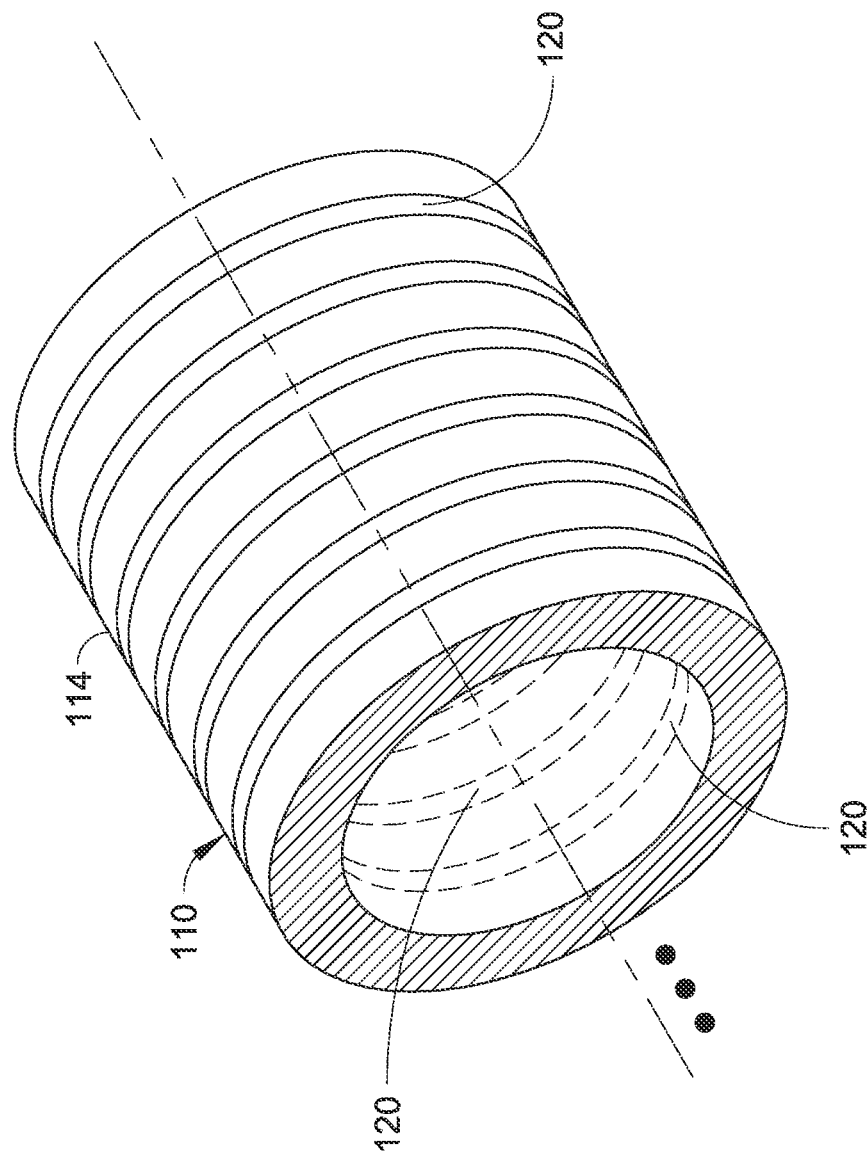
FIG. 6 is a partial cross-sectional isometric view illustrating a charged material transportation chamber with a patterned resistive trace deposited on an exterior surface of the charged material transportation chamber and/or a patterned resistive trace deposited on an interior surface of the charged material transportation chamber in accordance with an example implementation of the present disclosure.

As shown in FIG. 3, a resistive trace 120 can be configured as a helical resistive trace with multiple turns deposited adjacent to one another on the interior surface 116 of the tube 114. As used herein, the term "turn" is associated with the partial or complete circumferential travel of a segment of a patterned resistive trace with respect to the interior surface 116 of the tube 114 and/or the exterior surface 118 of the tube 114. In some implementations, a turn can be oriented at an angle from a perpendicular direction defined with respect to a longitudinal axis 126 of the tube 114 (e.g., in the case of the helical resistive traces 120 shown in FIGS. 3 and 6). Further, a turn can be oriented generally (e.g., at least substantially) perpendicular to the longitudinal axis 126 of the tube 114. For instance, as shown in FIGS. 4 and 5, resistive traces 120 can be configured with multiple turns deposited adjacent to one another on the interior surface 116 of the tube 114, where one or more of the turns are oriented at least substantially perpendicular to the longitudinal axis 126 of the tube 114. A turn can be associated with complete circumferential travel of a segment of a patterned resistive trace with respect to the interior surface 116 of the tube 114 (e.g., as shown in FIG. 3) and/or the exterior surface 118 of the tube 114 (e.g., as shown in FIG. 6). A turn can also be associated with partial circumferential travel of a segment of a patterned resistive trace with respect to the interior surface 116 of the tube 114 (e.g., as shown in FIG. 4 with turns of more than two hundred and seventy degrees (270°) but less than three hundred and sixty degrees (360°), and FIG. 5 with turns of less than two hundred and seventy degrees (270°)).

In embodiments of the disclosure, the number of turns can vary (e.g., depending upon the geometry of a particular chamber, operating voltage requirements, a desired uniformity for the generated electric field, and so forth). For example, a gap between adjacent turns of a resistive trace 120 may be limited by breakdown voltage. Further, the width of a resistive trace 120 can be determined based upon the angle between the resistive trace 120 and the longitudinal axis 126 of the tube 114. For example, a resistive trace 120 with a larger width may be used with a larger angle between the resistive trace 120 and the longitudinal axis 126 and produce a larger deflection of material trajectories. In this manner, gaps between turns/rings or their overlapping groups can be selected based upon a minimum distance to reliably withstand operating voltage, and widths of turns/rings or their overlapping groups can be selected based upon a maximum width to maintain substantial perpendicularity of the turns/rings or their overlapping groups with respect to the axis of the chamber. In one configuration, a resistive trace 120 can include eighteen (18) turns. In another configuration, a resistive trace 120 can include thirty-six (36) turns. In a further configuration, a resistive trace 120 can include seventy-two (72) turns. However, these configurations are provided by way of example only and are not meant to be restrictive of the present disclosure. Thus, in other configurations, a resistive trace 120 can include fewer than eighteen (18) turns, between eighteen (18) turns and thirty-six (36) turns, between thirty-six (36) turns and seventy-two (72) turns, more than seventy-two (72) turns, and so forth.

In some implementations, each turn of a patterned resistive trace is electrically connected to an adjacent turn in series. For example, as shown in FIG. 3, adjacent turns of the helical resistive trace 120 are connected to one another on the interior surface 116 of the tube 114. Referring now to FIGS. 4 and 5 adjacent turns of the resistive trace 120 can also be connected together using one or more jumpers 128. As shown in FIGS. 4 and 5, adjacent turns of the resistive trace 120 can be connected together using jumpers 128 deposited on the interior surface 116 of the tube 114.

Figure 8:
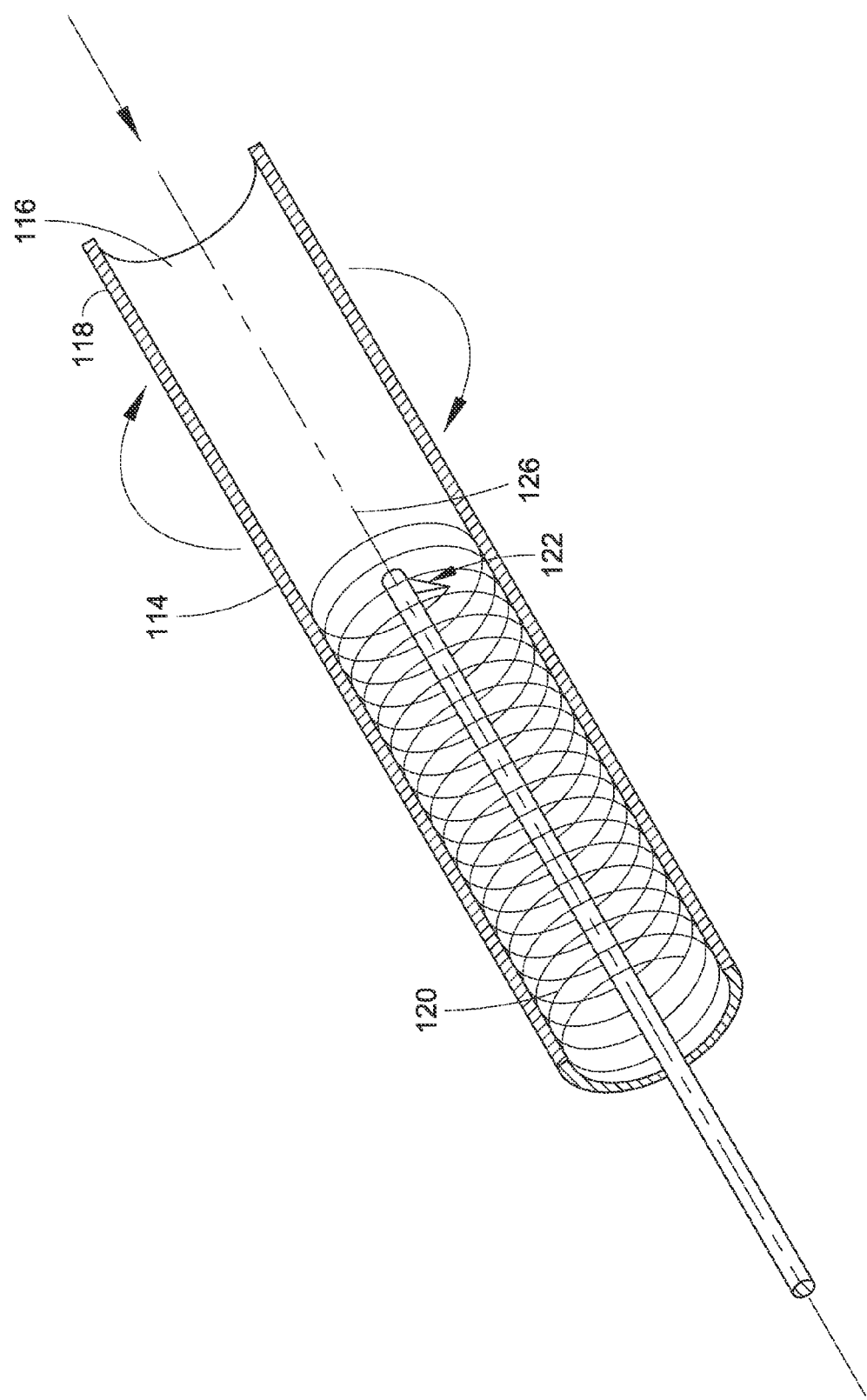
FIG. 8 is a partial cross-sectional isometric view illustrating a charged material transportation chamber with a helical resistive trace being deposited on an interior surface of the charged material transportation chamber, where the substrate is advanced longitudinally at a first rate in accordance with an example implementation of the present disclosure, and where a portion of the substrate is removed to illustrate the helical pattern of the resistive trace.

Referring generally to FIGS. 8 through 15B, an application tool can be used to apply various resistive trace patterns to the interior and/or exterior surfaces of a non-conductive or semi-conductive tube. In embodiments of the disclosure, relative motion of the tube and the application tool can be varied to create different resistive patterns. For example, as shown in FIG. 8, a conductive ink or film resistive trace 120 is applied to the interior surface 116 and/or the exterior surface 118 of the tube 114 by rotating the tube 114 at a controlled (e.g., at least substantially constant) rate, while the tube 114 is advanced longitudinally (e.g., horizontally) with respect to a stationary, or at least substantially stationary, application tool such as an ink application stylus 122. The motion of the tube 114 with respect to the ink application stylus 122 creates a pattern on the interior surface 116 and/or the exterior surface 118 of the tube 114.

As described herein, terms that refer to motion of the tube 114 and/or the ink application stylus 122, such as "rotating," "advancing," and so forth, are used to describe relative motion of the tube 114 with respect to the ink application stylus 122. Thus, in some embodiments, the tube 114 is rotated while the ink application stylus 122 is advanced. In other embodiments, the ink application stylus 122 is rotated while the tube 114 is advanced. In further embodiments, the tube 114 and the ink application stylus 122 are both rotated while one or both are advanced. In still further embodiments, the tube 114 and the ink application stylus 122 are both advanced while one or both are rotated. In further embodiments, the ink application stylus 122 is rotated and advanced while the tube 114 remains stationary, or at least substantially stationary, and so forth.

Figure 9:
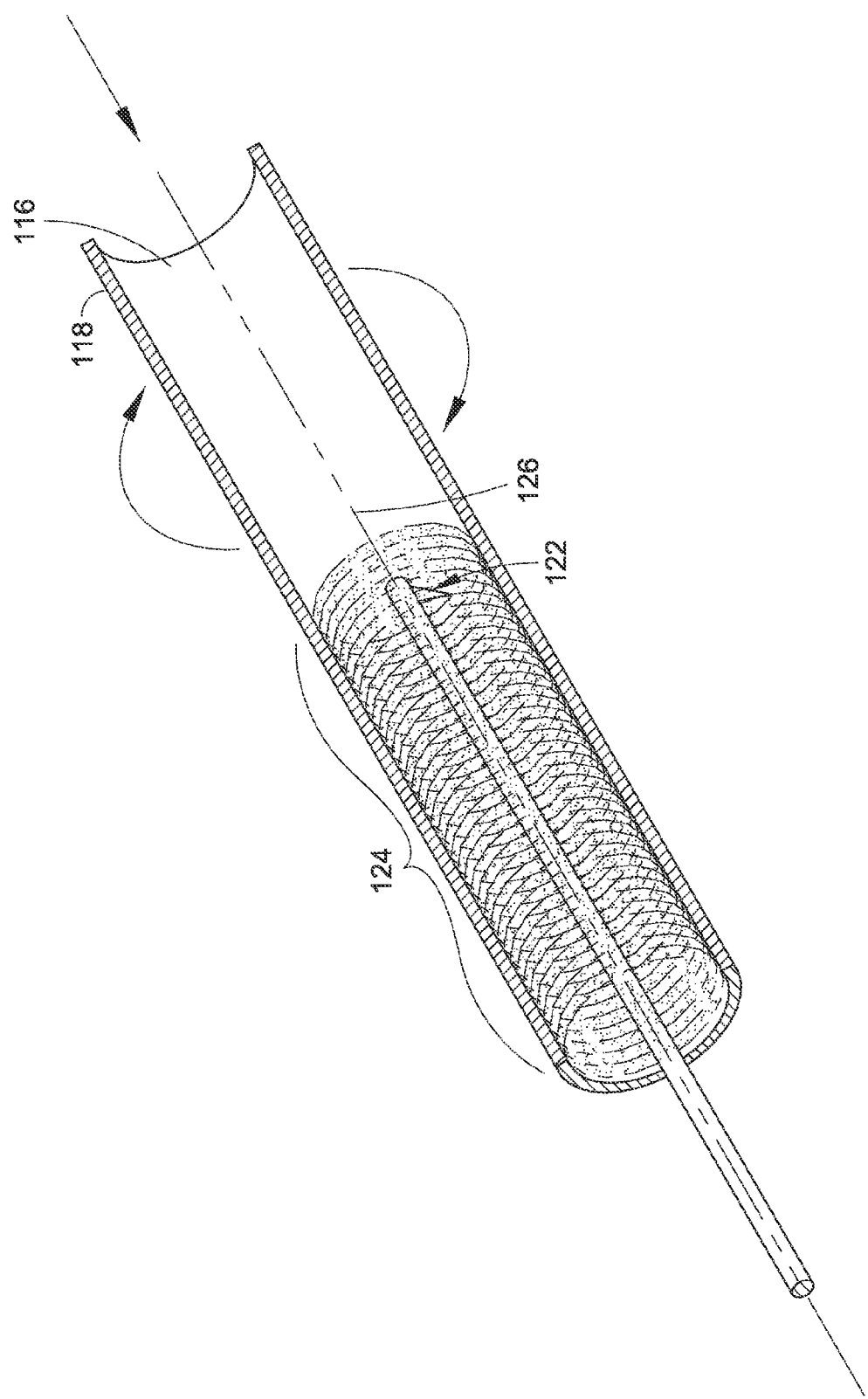
FIG. 9 is a partial cross-sectional isometric view illustrating a charged material transportation chamber with a helical resistive trace being deposited on an interior surface of the charged material transportation chamber, where the substrate is advanced longitudinally at a second rate in accordance with an example implementation of the present disclosure, and where a portion of the substrate is removed to illustrate the helical pattern of the resistive trace.

Different speeds and/or motion sequences for the tube 114 and/or the ink application stylus 122 are used to create different patterns on the tube 114. With reference to FIG. 9, a patterned resistive trace comprising a continuous conductive coating 124 is established between opposite ends of the tube 114 by rotating the tube 114 at a controlled rate while longitudinal motion of the tube 114 is very slow with respect to the rotational motion of the tube 114. This difference in the relative speeds of rotation and longitudinal motion creates a tightly wound conductive spiral. In some embodiments, adjacent segments of a resistive trace 120 overlap, resulting in the continuous conductive coating 124 on the interior surface 116 and/or the exterior surface 118 of the tube 114. Conductive inks and/or films with sufficiently high resistance can be deposited in this configuration to achieve a particular total drift tube resistance.

Figure 10:
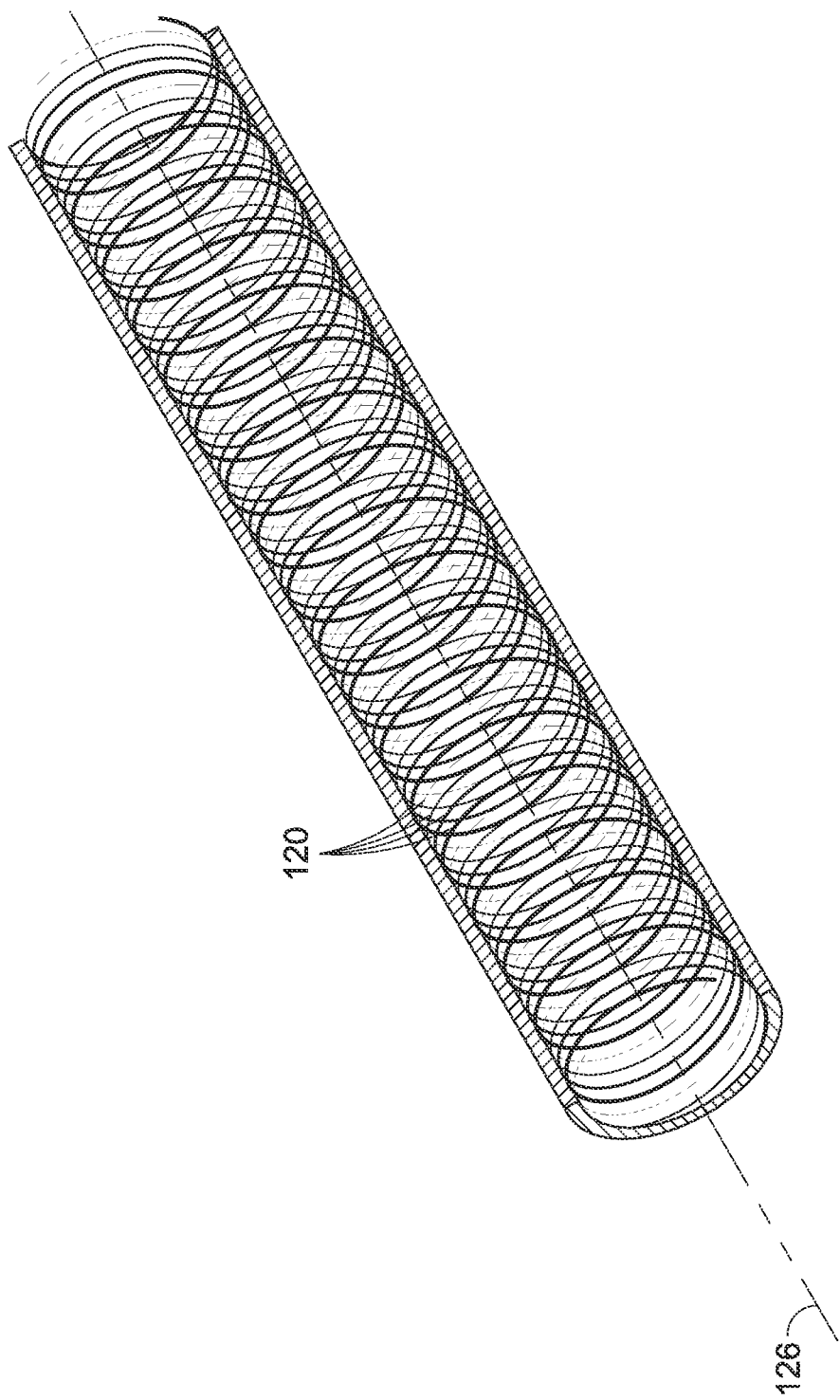
FIG. 10 is a partial cross-sectional isometric view illustrating a charged material transportation chamber with multiple helical resistive traces deposited on an interior surface of the charged material transportation chamber in accordance with an example implementation of the present disclosure, where a portion of the substrate is removed to illustrate the helical patterns of the resistive traces.

As shown in FIG. 10, multiple helical resistive traces 120 can be established on the tube 114 by repositioning the application tool at an end of the tube 114 at ninety degrees (90°), or another division of three hundred and sixty degrees (360°), with respect to the origin of a previous resistive trace 120 at the end of the tube 114. This technique can be used to create multiple resistive traces 120 substantially parallel to one another. In embodiments of the disclosure, the substantially parallel resistive traces 120 are used to provide greater symmetry at ends of the tube 114 (e.g., with respect to a single resistive trace 120).

Figure 11A:
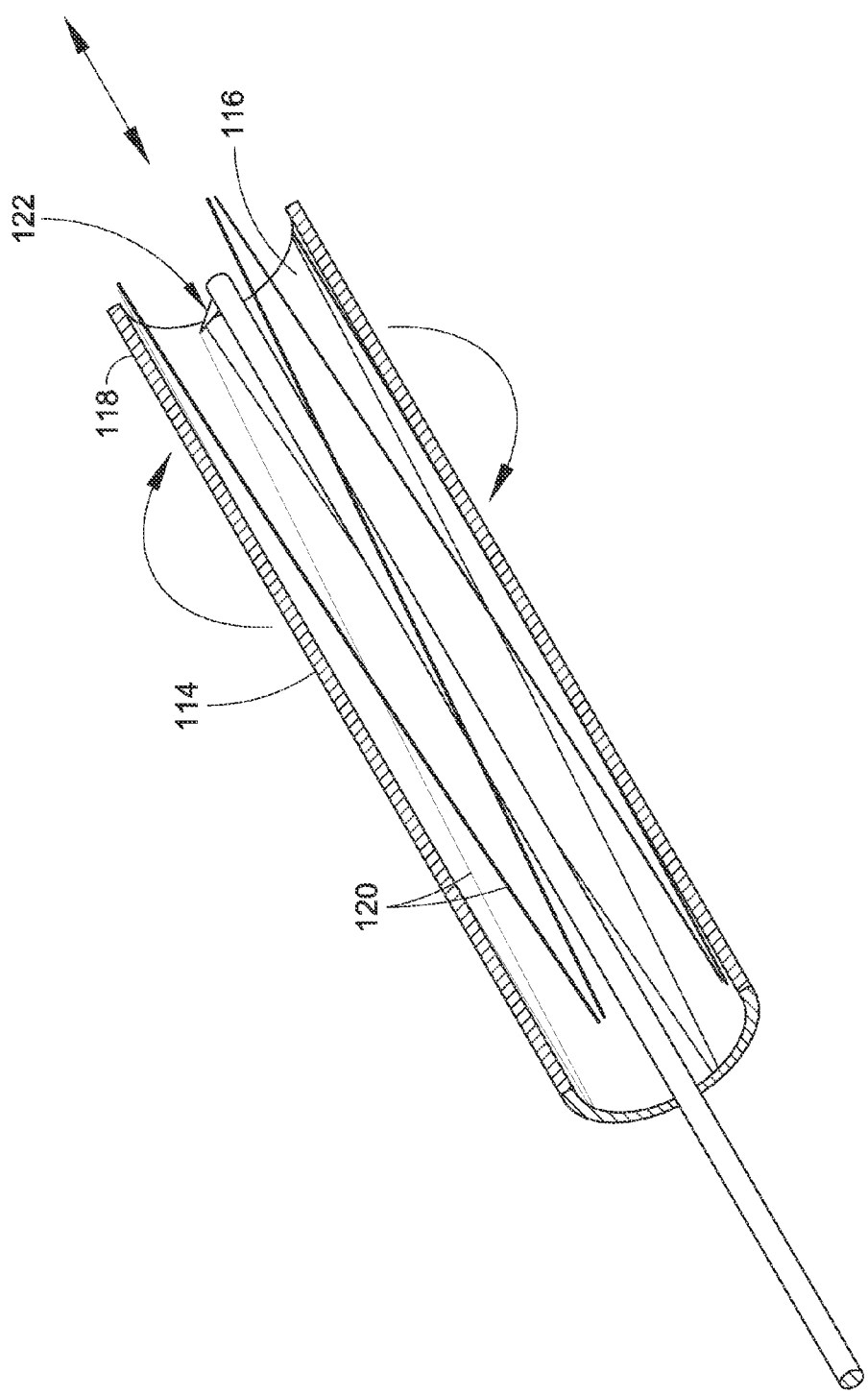
FIG. 11A is a partial cross-sectional isometric view illustrating a charged material transportation chamber with multiple patterned resistive traces being deposited on an interior surface of the charged material transportation chamber in accordance with an example implementation of the present disclosure, where a portion of the substrate is removed to illustrate the patterns of the resistive traces.
Figure 11B:
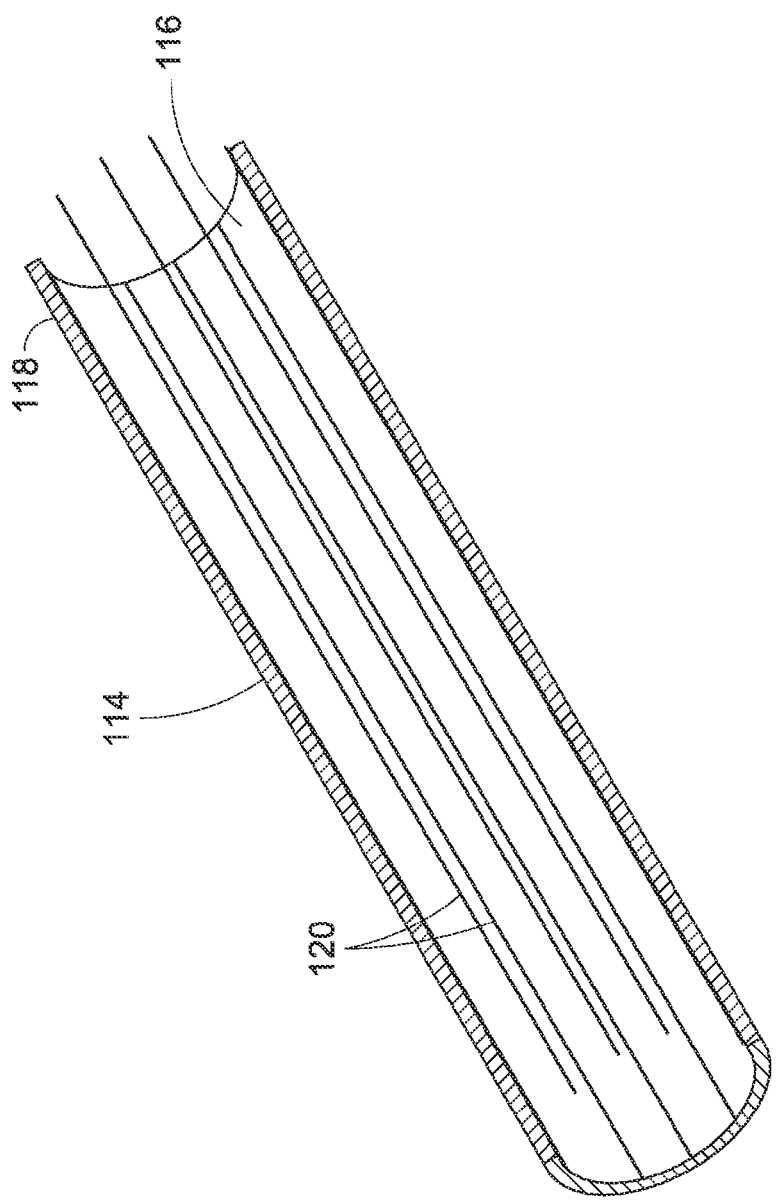
FIG. 11B is a partial cross-sectional isometric view illustrating a charged material transportation chamber with multiple patterned resistive traces deposited longitudinally on an interior surface of the charged material transportation chamber in accordance with an example implementation of the present disclosure, where a portion of the substrate is removed to illustrate the patterns of the resistive traces.

Referring to FIGS. 11A and 11B, multiple resistive traces 120 can be generated between ends of the tube 114. As shown in FIG. 11A, rotation of the tube 114 at a controlled (e.g., at least substantially constant) rate, with longitudinal motion at a relatively higher rate in a first direction, creates a slightly curved resistive trace 120 between the opposite ends of the tube 114. Then, longitudinal motion of the tube 114 in a second, opposite direction is used to establish another consecutive and somewhat parallel resistive trace 120 between the opposite ends of the tube 114. In this manner, a series of generally parallel resistive traces 120 are deposited between the ends of the tube 114. In other embodiments, parallel resistive traces 120 are established between opposite ends of the tube 114 (e.g., as shown in FIG. 11B). In embodiments of the disclosure, these techniques can be used to provide more consistent electrical connection between the ends of the tube 114 (e.g., with respect to a single resistive trace 120).

Figure 12:
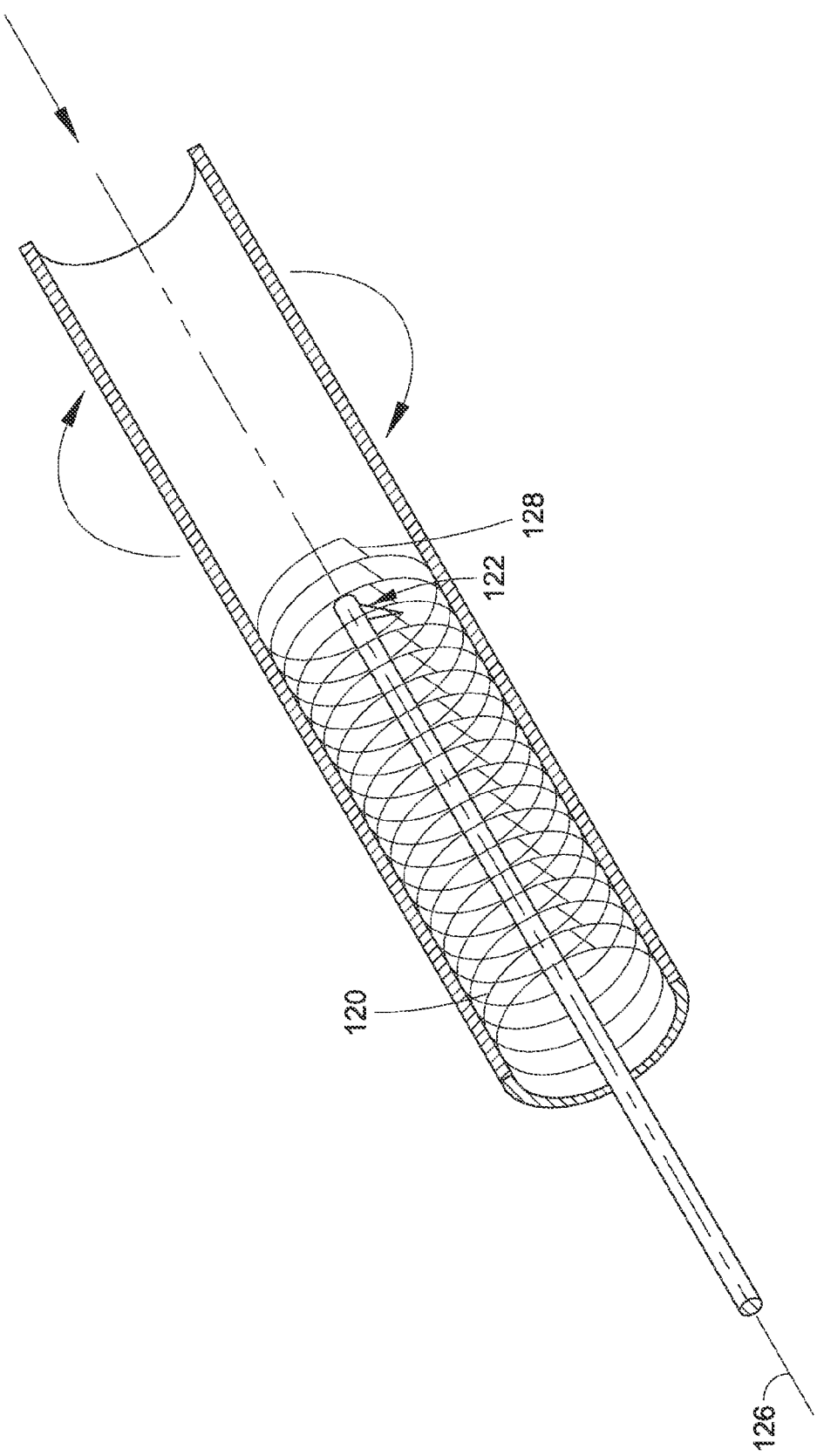
FIG. 12 is a partial cross-sectional isometric view illustrating a charged material transportation chamber with a patterned resistive trace being deposited on an interior surface of the charged material transportation chamber, where the substrate is advanced longitudinally at two different rates in accordance with an example implementation of the present disclosure, and where a portion of the substrate is removed to illustrate the pattern of the resistive trace.

As shown in FIG. 12, various patterns of trace configurations, such as the trace patterns shown in FIGS. 8 through 11, can be implemented together. In these configurations, rotation of the tube 114 at a controlled (e.g., at least substantially constant) rate with relatively slower longitudinal motion for a first period of time results in a turn of a resistive trace 120. The longitudinal motion of the tube 114 may also be stopped during the first period of time. This motion is followed by continued rotation of the tube 114 at the controlled rate with relatively faster longitudinal motion for a second (e.g., shorter) period of time, resulting in a single, slightly curved jumper 128. The rotation of the tube 114 may also be stopped during the second period of time, resulting in a substantially linear jumper 128. Then, rotation of the tube 114 at the controlled rate, with longitudinal motion at the relatively slower rate, results in another turn of the resistive trace 120. Again, this motion is followed by generation of another jumper 128, another turn of the resistive trace 120, and so on. In this manner, alternating sequences of slow and/or stopped, and relatively faster longitudinal motion of the tube 114 results in a series of turns of a resistive trace 120, connected to one another along the longitudinal axis 126 of the tube 114 with jumpers 128. In some embodiments, coaxial resistive turn portions of a resistive trace 120 are deposited using other methods, including but not necessarily limited to vacuum deposition, prior to using the ink application stylus 122 to deposit one or more jumpers 128 along the length of the tube 114 to connect the coaxial turn portions and increase the uniformity of the total resistance across the tube 114.

Figure 13A:
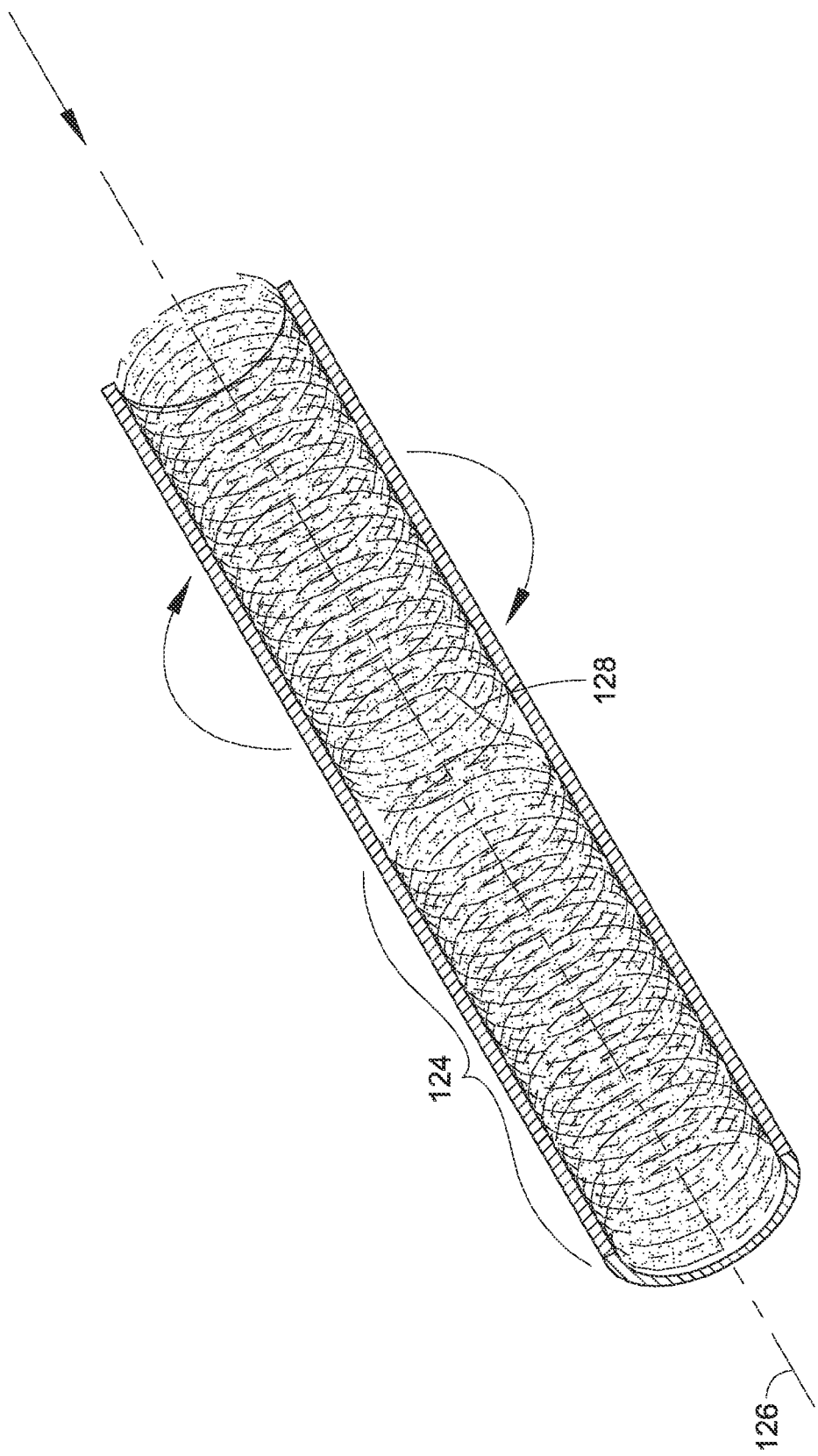
FIG. 13A is a partial cross-sectional isometric view illustrating a charged material transportation chamber with a patterned resistive trace deposited on an interior surface of the charged material transportation chamber, where the substrate is advanced longitudinally at two different rates in accordance with an example implementation of the present disclosure, and where a portion of the substrate is removed to illustrate the pattern of the resistive trace.
Figure 13B:
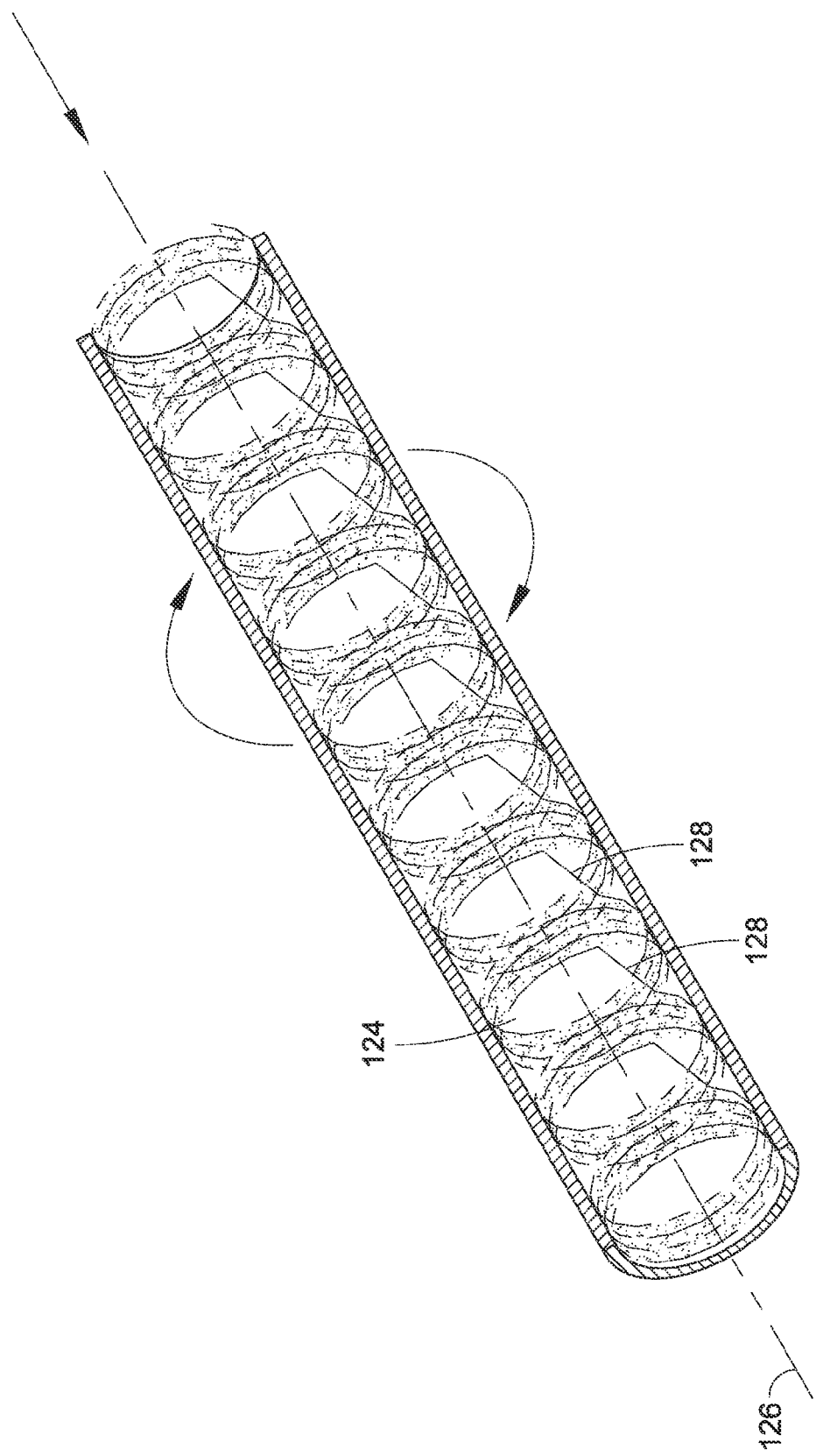
FIG. 13B is a partial cross-sectional isometric view illustrating a charged material transportation chamber with a patterned resistive trace deposited on an interior surface of the charged material transportation chamber, where the substrate is advanced longitudinally at two different rates in accordance with an example implementation of the present disclosure, and where a portion of the substrate is removed to illustrate the pattern of the resistive trace.

As shown in FIGS. 13A and 13B, additional combinations of the above approaches can be implemented in the form of a tightly wound patterned resistive trace comprising a continuous conductive coating 124 deposited at a comparatively slower longitudinal speed alternating with connecting jumpers 128 deposited at a comparatively higher longitudinal speed. FIG. 13A depicts two continuously coated portions connected with a single conductive jumper 128. FIG. 13B depicts several brief continuously coated portions connected with multiple jumpers 128. In some embodiments, e.g., to achieve at least substantial field uniformity, the width of the continuously coated portion and/or the width of a gap between the continuously coated portions are configured to approximate a particular pattern, such as the pattern described with reference to FIG. 12. In embodiments of the disclosure, the patterned resistive traces described in FIGS. 13A and 13B can be used to create a stepped electric field for moving ions, where each jumper 128 creates a resistive drop between adjacent portions of the continuous conductive coating 124. For example, a voltage drop can be created between adjacent continuously coated portions by the higher resistance of a jumper 128 with respect to the continuous conductive coating 124 (e.g., due to the reduced cross-sectional area of the jumper 128 with respect to the continuous conductive coating 124). Further, the patterned resistive traces can be applied using a resistive ink via high pressure delivery through an application tool, such as a stainless steel needle. The motion of the tube 114 and/or the application tool can be controlled using, for example, one or more stepper motors.

Figure 14B:
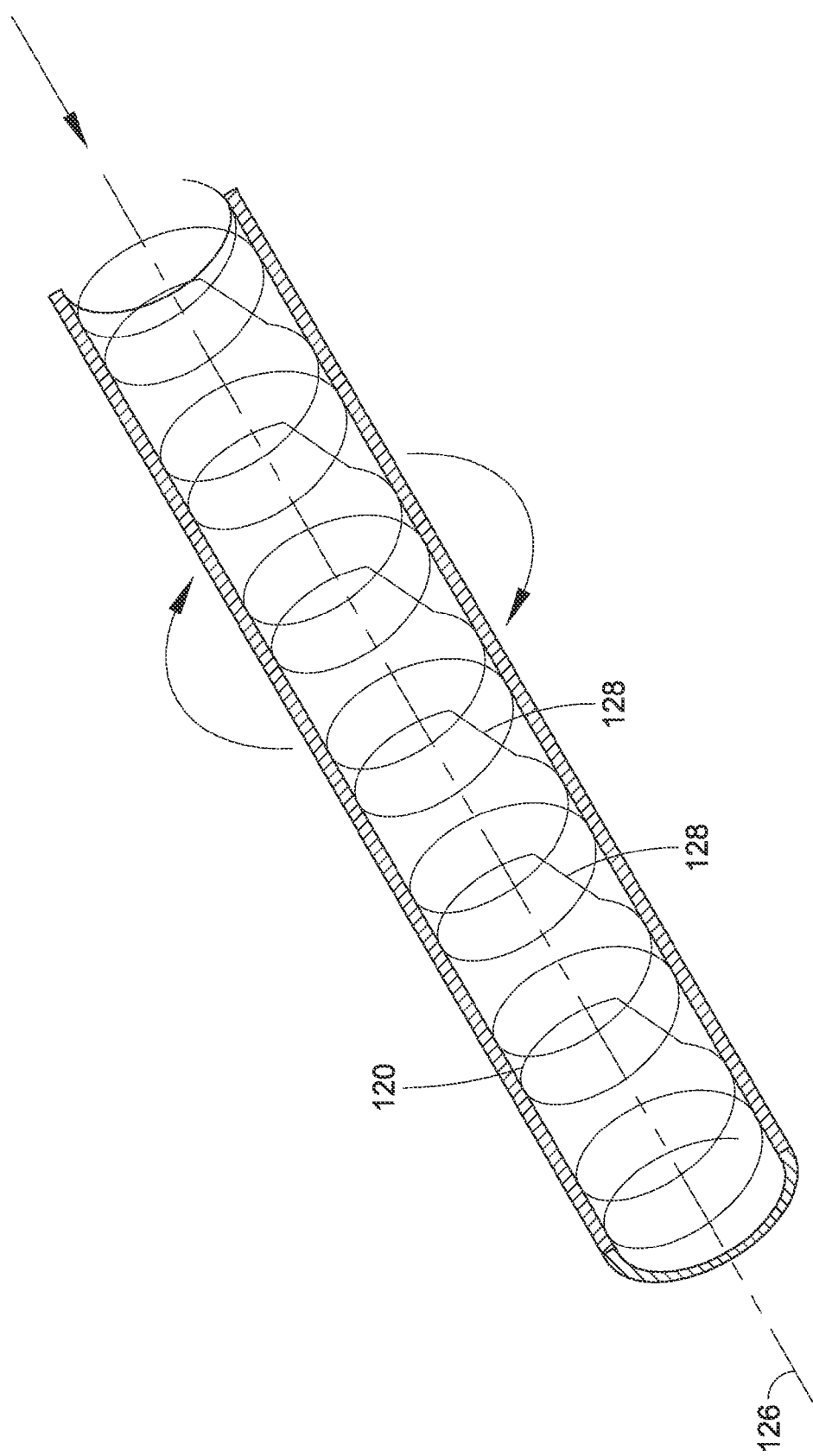
FIG. 14B is a partial cross-sectional isometric view illustrating a charged material transportation chamber with a patterned resistive trace deposited on an interior surface of the charged material transportation chamber, where the substrate is advanced longitudinally at two different rates in accordance with an example implementation of the present disclosure, and where a portion of the substrate is removed to illustrate the pattern of the resistive trace.

Referring now to FIGS. 14A and 14B, additional combinations of previously described approaches can be implemented in the form of a patterned resistive trace comprising loosely wound helical resistive traces 120, which can be deposited at a moderate longitudinal speed alternating with jumpers 128. FIG. 14A depicts two large helical resistive trace portions connected with jumpers 128. FIG. 14B depicts several brief helical resistive trace portions connected with jumpers 128.

Figure 15B:
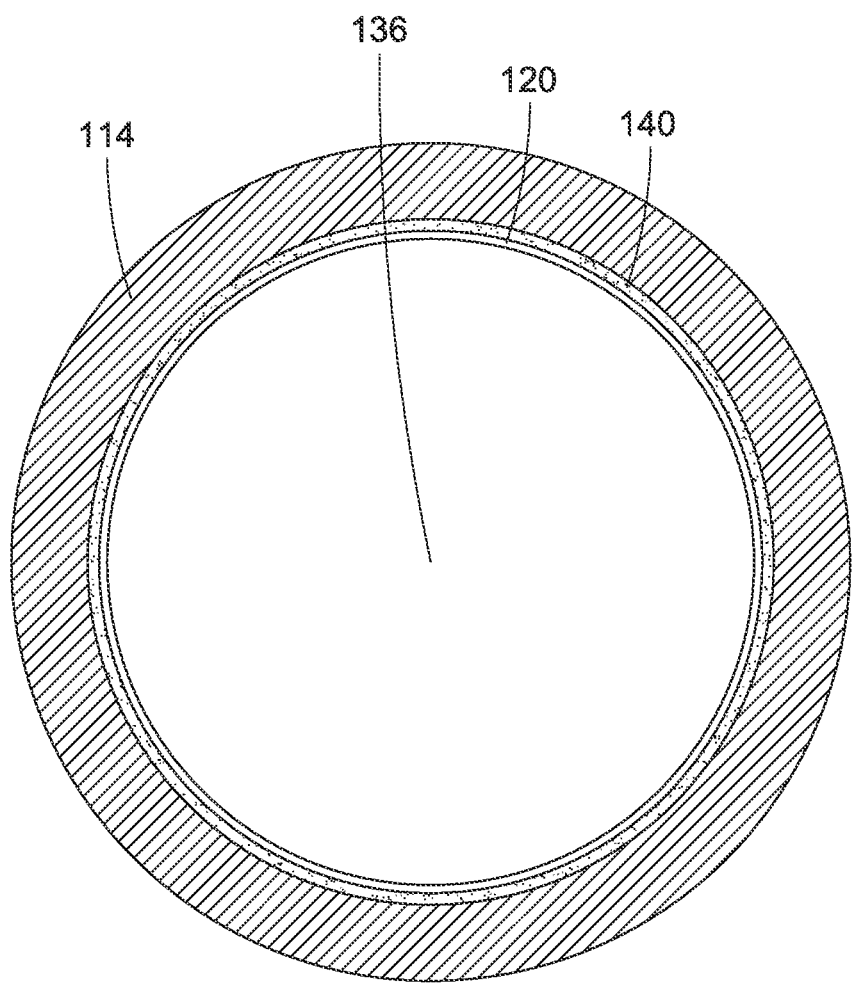
FIG. 15B is a cross-sectional end view of the charged material transportation chamber illustrated in FIG. 15A.

As shown in FIGS. 15A and 15B, the tube 114 can also have a primary continuous conductive coating 140 applied on its interior surface 116 and/or exterior surface 118, over which a secondary resistive trace 120 can be applied. The secondary resistive trace 120 can be helical or any combination of patterns depicted in, for instance, the preceding figures. In this configuration, one or more resistive traces 120 can reduce and/or minimize electric field distortions caused by resistive and/or physical imperfections in the uniformity of the primary continuous conductive coating 140. Further, the primary continuous conductive coating 140 can reduce and/or minimize the influence of external electric fields on the interior of the tube 114, which acts as the drift region 136. In some embodiments, the total resistance of the primary continuous conductive coating 140 across the tube 114 is greater than the resistance of the secondary resistive trace 120. For example, the resistance of the primary continuous conductive coating 140 can be about five hundred mega ohms (500 MΩ), and the resistance of the resistive trace 120 can range between about twenty mega ohms (20 MΩ) and two hundred mega ohms (200 MΩ).

Figure 16:
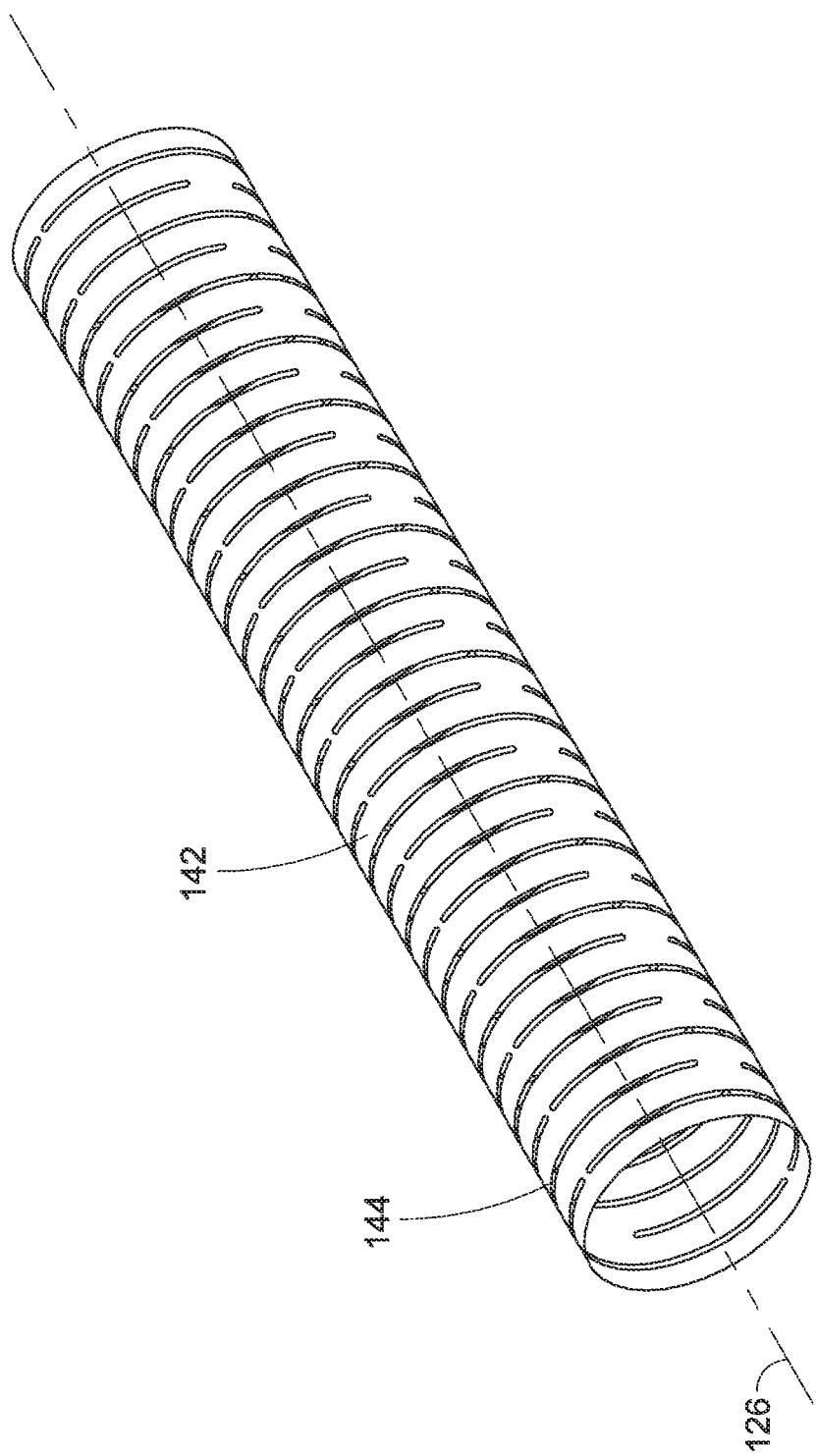
FIG. 16 is a partial isometric view illustrating a charged material transportation chamber with a patterned resistive trace deposited on an interior surface of the charged material transportation chamber in accordance with an example implementation of the present disclosure, where a portion of the substrate is removed to illustrate the pattern of the resistive trace.
Figure 17:
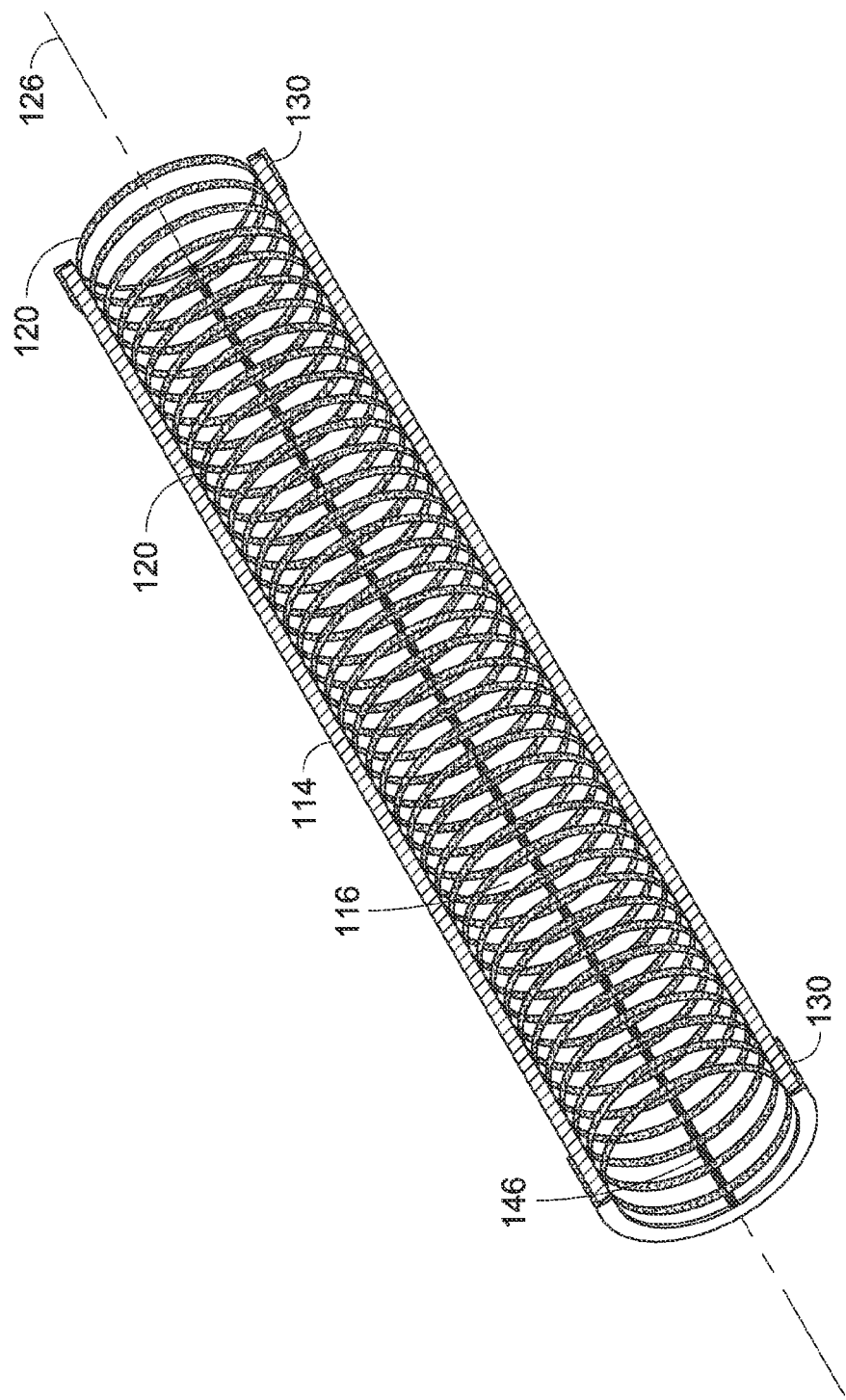
FIG. 17 is a partial cross-sectional isometric view illustrating a charged material transportation chamber with a series of concentric resistive traces applied to an interior surface of the charged material transportation chamber and linked by a longitudinal resistive trace, where the longitudinal resistive trace is in electrical contact with opposite ends of the charged material transportation chamber in accordance with an example implementation of the present disclosure, and where a portion of the substrate is removed to illustrate the patterns of the resistive traces.
Figure 18:
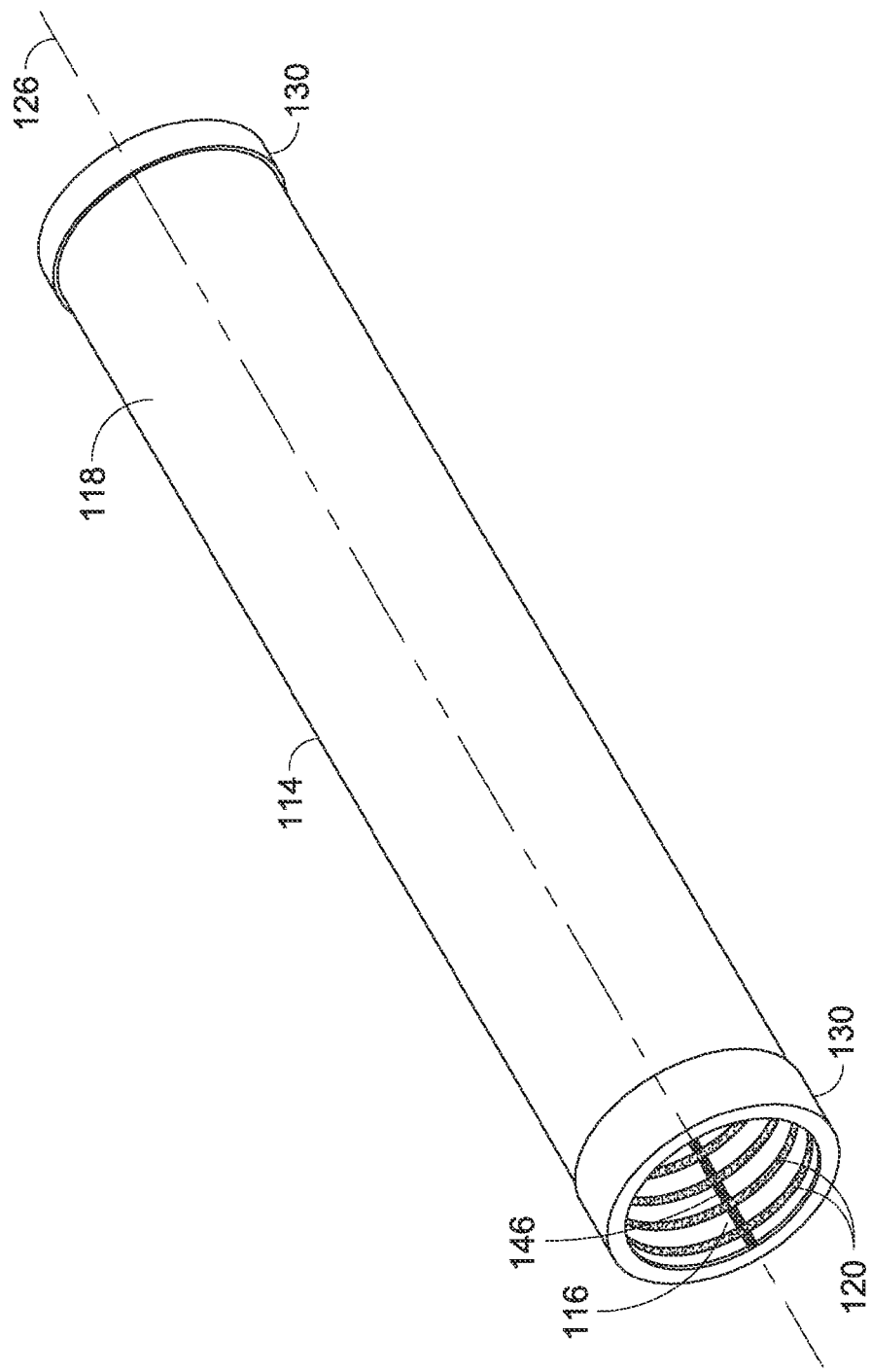
FIG. 18 is an isometric view of the charged material transportation chamber illustrated in FIG. 17.
Figure 19:
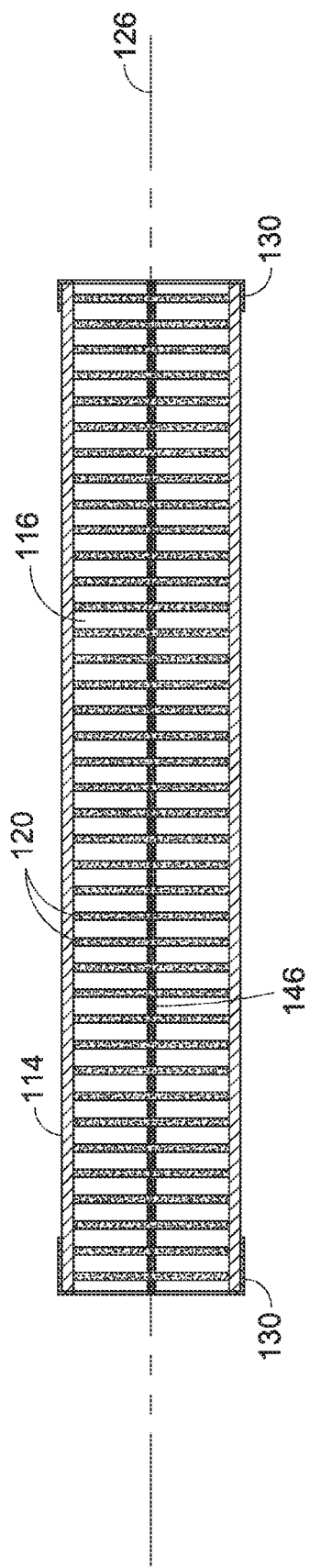
FIG. 19 is a cross-sectional side elevation view of the charged material transportation chamber illustrated in FIG. 17.

Referring now to FIG. 16, in some embodiments the tube 114 includes a patterned resistive layer 142 comprising one or more apertures (e.g., slots 144) oriented in directions generally (e.g., at least substantially) perpendicular to the longitudinal axis 126 of the tube 114. In embodiments of the disclosure, the apertures are configured to reduce or minimize radial electric field caused by potential electrical asymmetry of, for instance, a continuous layer. In the configuration shown in FIG. 16, the slots 144 are axially interleaved. However, this configuration is provided by way of example only and is not meant to limit the present disclosure. In other embodiments, the slots 144 can be shaped and/or aligned differently.

In some embodiments a tube 114 has multiple resistive traces 120 (e.g., conductive rings) applied to its interior surface 116 and/or exterior surface 118, and the resistive traces 120 are linked (e.g., connected) using one or more longitudinal resistive traces 146. For example, as shown in FIGS. 17 through 20, resistive traces 120 configured as a series of concentric resistive ink rings are applied to the interior surface 116 of the tube 114. The resistive traces 120 are then linked by a longitudinal resistive trace 146 configured as a generally straight, longitudinal resistive ink trace connected between, for example, two connectors 130 disposed on the tube 114. For example, the longitudinal resistive trace 146 is in electrical contact with metalized ends of the tube 114. However, it should be noted that the concentric resistive ink rings and the generally straight, longitudinal resistive ink trace are provided by way of example only and are not meant to limit the present disclosure. In other embodiments, differently configured resistive traces 120 and/or longitudinal resistive traces 146 are used. For example, a longitudinal resistive trace 146 can be slightly curved, sinusoidal, and so forth. Further, one or more of the resistive traces 120 can be helical or any combination of patterns depicted in, for instance, the preceding figures.

Figure 20:
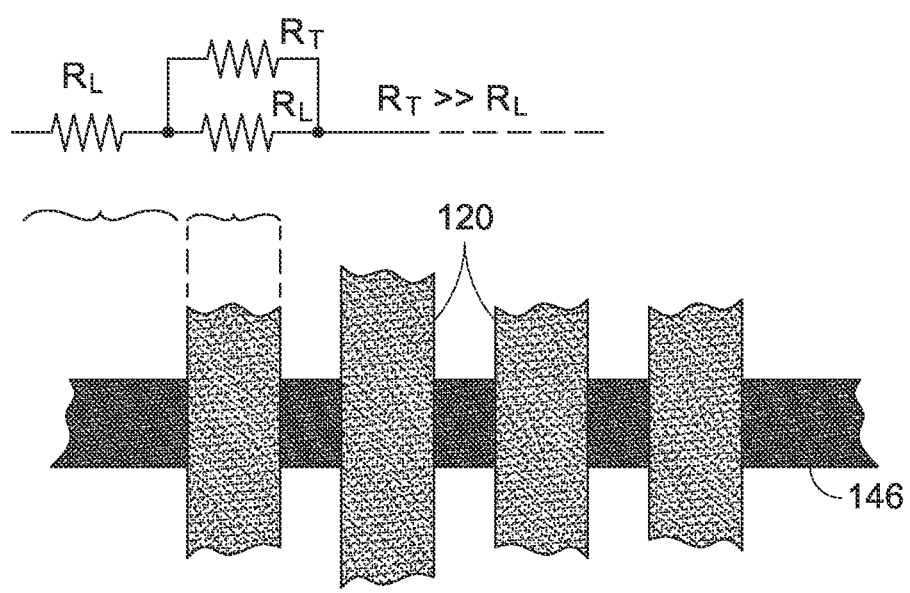
FIG. 20 is a diagrammatic illustration of multiple resistive traces linked by a longitudinal resistive trace in accordance with an example implementation of the present disclosure, further illustrating resistances of the multiple resistive traces and the longitudinal resistive trace.

In some embodiments, the resistivity of the ink comprising the concentric rings is greater than (e.g., substantially greater than) the resistivity of the ink comprising the straight, continuous trace. For example, the total resistance of the generally straight, longitudinal resistive ink trace on its own is about one hundred mega ohms (100 MΩ). This configuration can be used to reduce (e.g., minimize) the effect of the additional parallel resistance applied across the generally straight, longitudinal resistive ink trace (e.g., as shown in FIG. 20). However, this resistance value is provided by way of example only and is not meant to limit the present disclosure. In other embodiments, the total resistance of the generally straight, longitudinal resistive ink trace can be greater than or less than about one hundred mega ohms.

In some configurations, one or more patterned resistive traces deposited on an exterior surface 118 of the tube 114 are electrically connected to one or more patterned resistive traces deposited on an interior surface 116 of the tube 114. For example, jumpers 128 can be used to connect a resistive trace 120 deposited on the interior surface 116 of the tube 114 to one or more resistive traces 120 deposited on the exterior surface 118 of the tube 114 (e.g., connected in series). However, this configuration is provided by way of example only and is not meant to be restrictive of the present disclosure. In other implementations, one or more resistive traces 120 deposited on the exterior surface 118 of the tube 114 and one or more resistive traces 120 deposited on the interior surface 116 of the tube 114 are separately connected (e.g., connected in parallel).

In some configurations, the length of the tube 114 is between at least approximately two centimeters (2 cm) and fifteen centimeters (15 cm). The diameter of the interior surface 116 of the tube 114 can be between at least approximately two and one-half millimeters (2.5 mm) and twenty-five millimeters (25 mm). Further, the diameter of the exterior surface 118 of the tube 114 can be between at least approximately three millimeters (3 mm) and thirty millimeters (30 mm). However, these dimensions are provided by way of example only and are not meant to be restrictive of the present disclosure. Thus, in other configurations, the length of the tube 114 may be less than at least approximately two centimeters (2 cm) or greater than at least approximately fifteen centimeters (15 cm). The diameter of the interior surface 116 of the tube 114 may be less than at least approximately two and one-half millimeters (2.5 mm) or greater than at least approximately twenty-five millimeters (25 mm). Further, the diameter of the exterior surface 118 of the tube 114 may be less than at least approximately three millimeters (3 mm) or greater than at least approximately thirty millimeters (30 mm).

The width of a patterned resistive trace (e.g., as measured in a generally longitudinal direction parallel to the longitudinal axis 126 of the tube 114) can be between at least approximately one-tenth of one millimeter (0.1 mm) and one millimeter (1 mm). For example, the width of the resistive trace 120 can be at least approximately twenty one-thousandths of one inch (0.020"). In some configurations, the resistive trace 120 has at least approximately two turns per centimeter. For example, the pitch of a patterned resistive trace, which can be defined as the spacing between the centerlines of the deposited material forming adjacent turns of the patterned resistive trace, can be between at least approximately one-tenth of one millimeter (0.1 mm) and one millimeter (1 mm). For example, the pitch of the resistive trace 120 can be at least approximately twenty-eight one-thousandths of one inch (0.028"). However, these dimensions are provided by way of example only and are not meant to be restrictive of the present disclosure. Thus, in other configurations, the width of a patterned resistive trace can be less than at least approximately one-tenth of one millimeter (0.1 mm) or greater than one millimeter (1 mm). The resistive trace 120 can have more or fewer than at least approximately two turns per centimeter. Further, the pitch of a patterned resistive trace can be less than at least approximately one-tenth of one millimeter (0.1 mm) or greater than at least approximately one millimeter (1 mm).

In some instances, one or more characteristics of the resistive traces 120 can be generally consistent throughout the length of the tube 114. For example, the pitch of the resistive trace 120 can be generally constant throughout the length of the tube 114. In other instances, one or more characteristics of the resistive traces 120 can vary throughout the length of the tube 114. For instance, the pitch between adjacent turns of a patterned resistive trace can vary through the tube 114 (e.g., increasing and/or decreasing). The width and/or thickness of a patterned resistive trace can also vary throughout the length of the tube 114.

One or more of the resistive traces 120 is configured to connect to a source of electrical energy to energize the resistive trace and establish an electric field. For example, one or more of the resistive traces 120 are formed using thick film deposition to form an electrically resistive conductor. In some implementations, when energized, a substantially uniform electric field is established within the tube 114. In implementations, the electric field is a high voltage (HV) electric field, which can be used to control movement of ionized materials through the tube 114 (e.g., in the manner of a drift region/chamber). However, a substantially uniform electric field is provided by way of example only and is not meant to be restrictive of the present disclosure. For example, a shaped electric field can be established within the tube 114. In an example implementation, the shaped electric field varies in intensity (e.g., varying from lower intensity to higher intensity) along the length of the tube 114. In some implementations, one or more of the resistive traces 120 can be an ion modifier, which can be used to separate ions that would otherwise have similar mobility. For instance, one or more resistive traces 120 configured as an ion modifier can be used to fragment ions and alter the mobility of the ions, the mass to charge ratio of the ions, and so forth.

One or both ends of the drift tube 110 can include a connector 130. For example, an end of the drift tube 110 can be capped with a flange coated with conductive material (e.g., a metalized conductive flange). One or more of the resistive traces 120 can electrically connect to the connector 130, which can be connected to a source of electrical energy (e.g., a power supply) to energize a resistive trace and establish an electric field. However, a conductive flange is provided by way of example only and is not meant to be restrictive of the present disclosure. In other implementations, one or more of the resistive traces 120 can be connected to a source of electrical energy using other connectors including, but not necessarily limited, to a conductive cap, a conductive coating, and so forth. When energized, the drift tube 110 can be used to provide controllable transportation of charged materials (e.g., ions) from one end of the drift tube 110 to the other end of the drift tube 110.

The inlet 104 can employ a variety of sample introduction approaches. In some instances, a flow of air can be used. In other instances, IMS systems 100 can use a variety of fluids and/or gases to draw material into the inlet 104. Approaches for drawing material through the inlet 104 include the use of fans, pressurized gases, a vacuum created by a drift gas flowing through a drift region/chamber, and so forth. For example, the sample detector 102 can be connected to a sampling line, where air from the surrounding environment (e.g., room air) is drawn into the sampling line using a fan. IMS systems 100 can operate at substantially ambient pressure, although a stream of air or other fluid can be used to introduce sample material into a reaction region. In other instances, IMS systems 100 can operate at lower pressures (i.e., pressures less than ambient pressure). Further, IMS systems 100 can include other components to furnish introduction of material from a sample source. For example, a desorber, such as a heater, can be included with an IMS system 100 to cause at least a portion of a sample to vaporize (e.g., enter its gas phase) so the sample portion can be drawn into the inlet 104. For instance, a sample probe, a swab, a wipe, or the like, can be used to obtain a sample of interest from a surface. The sample probe can then be used to deliver the sample to the inlet 104 of an IMS system 100. IMS systems 100 can also include a pre-concentrator to concentrate or cause a bolus of material to enter a reaction region.

A portion of a sample can be drawn through an inlet 104 configured as a small aperture inlet (e.g., a pinhole) into the sample detector 102 using, for example, a diaphragm in fluid communication with an interior volume of the sample detector 102. For instance, when the internal pressure in the interior volume is reduced by movement of the diaphragm, a portion of the sample is transferred from the inlet 104 into the sample detector 102 through the pinhole. After passing through the pinhole, the sample portion enters the inlet assembly 108. The inlet assembly 108 can include a reaction chamber 132 where the sample is ionized using an ionization source, such as a corona discharge ionizer (e.g., having a corona discharge point), and possibly modified (e.g., using one or more reactants). However, a corona discharge ionizer is provided by way of example only and is not meant to be restrictive of the present disclosure. Other example ionization sources include, but are not necessarily limited to: radioactive and electrical ionization sources, such as a photoionization source, an electrospray source, a matrix assisted laser desorption ionization (MALDI) source, a nickel-63 source ($^{63}$Ni), an americium-241 source ($^{241}$Am), and so forth. In some instances, the ionization source can ionize material from a sample of interest in multiple steps. For example, the ionization source can generate a corona that ionizes gases in the reaction chamber 132 that are subsequently used to ionize the material of interest. Example gases include, but are not necessarily limited to: nitrogen, water vapor, gases included in air, and so forth.

In implementations, the inlet assembly 108 can operate in positive mode, negative mode, switch between positive and negative mode, and so forth. For example, in positive mode the ionization source can generate positive ions from a sample of interest, while in negative mode the ionization source can generate negative ions. Operation of the inlet assembly 108 in positive mode, negative mode, or switching between positive and negative mode can depend on implementation preferences, a predicted sample type (e.g., explosive, narcotic, toxic industrial chemicals), and so forth. Further, the ionization source can be pulsed periodically (e.g., based upon sample introduction, gate opening, the occurrence of an event, and so on).

The sample ions can then be directed toward a gating assembly using an electric field (e.g., generated in the same way or a similar way as in the drift chamber previously described). The gating assembly includes one or more (e.g., two) gating grids and can be opened momentarily to allow small clusters of sample ions to enter a drift region. For example, the inlet assembly 108 can include an electronic shutter or gate 134 at the inlet end of a drift region 136. In implementations, the gate 134 controls entrance of ions to the drift region 136. For example, the gate 134 can include a mesh of wires to which an electrical potential difference is applied or removed. The drift region 136 has electrodes (e.g., focusing rings formed by one or more of the resistive traces 120) spaced along its length for producing an electric field to draw ions along the drift region 136 and/or to direct the ions toward a detector disposed generally opposite the gate 134 in the drift region 136. For example, the drift region 136, including the electrodes, can create a substantially uniform field in the drift region 136. The sample ions can be collected at a collector electrode, which can be connected to analysis instrumentation for analyzing the flight times of the various sample ions. For instance, a collector plate 138 at the far end of the drift region 136 can collect ions that pass along the drift region 136.

The drift tube 110 can be used to separate ions admitted to the drift region 136 based on the individual ions' ion mobility. Ion mobility is determined by the charge on an ion, an ion's mass, geometry, and so forth. In this manner, IMS systems 100 can separate ions based on time of flight. The drift region 136 can have a substantially uniform electrical field that extends from the gate 134 to a collector. The collector can be a collector plate 138 (e.g., a Faraday plate) that detects ions based on their charge as they contact the collector plate 138. In implementations, a drift gas can be supplied through the drift region 136 in a direction generally opposite the ions' path of travel to the collector plate 138. For example, the drift gas can flow from adjacent the collector plate 138 toward the gate 134. Example drift gases include, but are not necessarily limited to: nitrogen, helium, air, air that is re-circulated (e.g., air that is cleaned and/or dried) and so forth. For example, a pump can be used to circulate air along the drift region 136 against the direction of flow of ions. The air can be dried and cleaned using, for instance, a molecular sieve pack.

In implementations, the sample detector 102 can include a variety of components to promote identification of a material of interest. For example, the sample detector 102 can include one or more cells containing a calibrant and/or a dopant component. Calibrant can be used to calibrate the measurement of ion mobility. Dopant can be used to selectively ionize molecules. Dopant can also be combined with a sample material and ionized to form an ion that can be more effectively detected than an ion that corresponds to the sample material alone. Dopant can be provided to one or more of the inlet 104, the reaction chamber 132, and/or the drift region 136. The sample detector 102 can be configured to provide dopant to different locations, possibly at different times during operation of the sample detector 102. The sample detector 102 can be configured to coordinate dopant delivery with operation of other components of an IMS system 100.

A controller can detect the change in charge on the collector plate 138 as ions reach it. Thus, the controller can identify materials from their corresponding ions. In implementations, the controller can also be used to control opening of the gate 134 to produce a spectrum of time of flight of the different ions along the drift region 136. For example, the controller can be used to control voltages applied to the gate 134. Operation of the gate 134 can be controlled to occur periodically, upon the occurrence of an event, and so forth. For example, the controller can adjust how long the gate 134 is open and/or closed based upon the occurrence of an event (e.g., corona discharge), periodically, and so forth. Further, the controller can switch the electrical potential applied to the gate 134 based upon the mode of the ionization source (e.g., whether the inlet assembly 108 is in positive or negative mode). In some instances, the controller can be configured to detect the presence of explosives and/or chemical agents and provide a warning or indication of such agents on an indicator.

In implementations, an IMS system 100, including some or all of its components, can operate under computer control. For example, a processor can be included with or in an IMS system 100 to control the components and functions of IMS systems 100 described herein using software, firmware, hardware (e.g., fixed logic circuitry), manual processing, or a combination thereof. The terms "controller" "functionality," "service," and "logic" as used herein generally represent software, firmware, hardware, or a combination of software, firmware, or hardware in conjunction with controlling the IMS systems 100. In the case of a software implementation, the module, functionality, or logic represents program code that performs specified tasks when executed on a processor (e.g., CPU or CPUs). The program code may be stored in one or more computer-readable memory devices (e.g., internal memory and/or one or more tangible media), and so on. The structures, functions, approaches, and techniques described herein can be implemented on a variety of commercial computing platforms having a variety of processors.

For example, the sample detector 102 may be coupled with the controller for controlling the energy supplied to the resistive traces 120. The controller may include a processing module, a communications module, and a memory module. The processing module provides processing functionality for the controller and may include any number of processors, micro-controllers, or other processing systems, and resident or external memory for storing data and other information accessed or generated by the controller. The processing module may execute one or more software programs, which implement techniques described herein. The processing module is not limited by the materials from which it is formed or the processing mechanisms employed therein, and as such, may be implemented via semiconductor(s) and/or transistors (e.g., using electronic integrated circuit (IC) components), and so forth. The communications module is operatively configured to communicate with components of the sample detector 102. The communications module is also communicatively coupled with the processing module (e.g., for communicating inputs from the sample detector 102 to the processing module). The communications module and/or the processing module can also be configured to communicate with a variety of different networks, including, but not necessarily limited to: the Internet, a cellular telephone network, a local area network (LAN), a wide area network (WAN), a wireless network, a public telephone network, an intranet, and so on.

The memory module is an example of tangible computer-readable media that provides storage functionality to store various data associated with operation of the controller, such as software programs and/or code segments, or other data to instruct the processing module and possibly other components of the controller to perform the steps described herein. Thus, the memory can store data, such as a program of instructions for operating the IMS system 100 (including its components), spectral data, and so on. Although a single memory module is shown, a wide variety of types and combinations of memory (e.g., tangible memory, non-transitory) may be employed. The memory module may be integral with the processing module, may include stand-alone memory, or may be a combination of both.

The memory module may include, but is not necessarily limited to: removable and non-removable memory components, such as Random Access Memory (RAM), Read-Only Memory (ROM), Flash memory (e.g., a Secure Digital (SD) memory card, a mini-SD memory card, and/or a micro-SD memory card), magnetic memory, optical memory, Universal Serial Bus (USB) memory devices, hard disk memory, external memory, and other types of computer-readable storage media. In implementations, the sample detector 102 and/or memory module may include removable Integrated Circuit Card (ICC) memory, such as memory provided by a Subscriber Identity Module (SIM) card, a Universal Subscriber Identity Module (USIM) card, a Universal Integrated Circuit Card (UICC), and so on.

In implementations, a variety of analytical devices can make use of the structures, techniques, approaches, and so on described herein. Thus, although IMS systems 100 are described herein, a variety of analytical instruments may make use of the described techniques, approaches, structures, and so on. These devices may be configured with limited functionality (e.g., thin devices) or with robust functionality (e.g., thick devices). Thus, a device's functionality may relate to the device's software or hardware resources, e.g., processing power, memory (e.g., data storage capability), analytical ability, and so on.

Example Process

Figure 7:
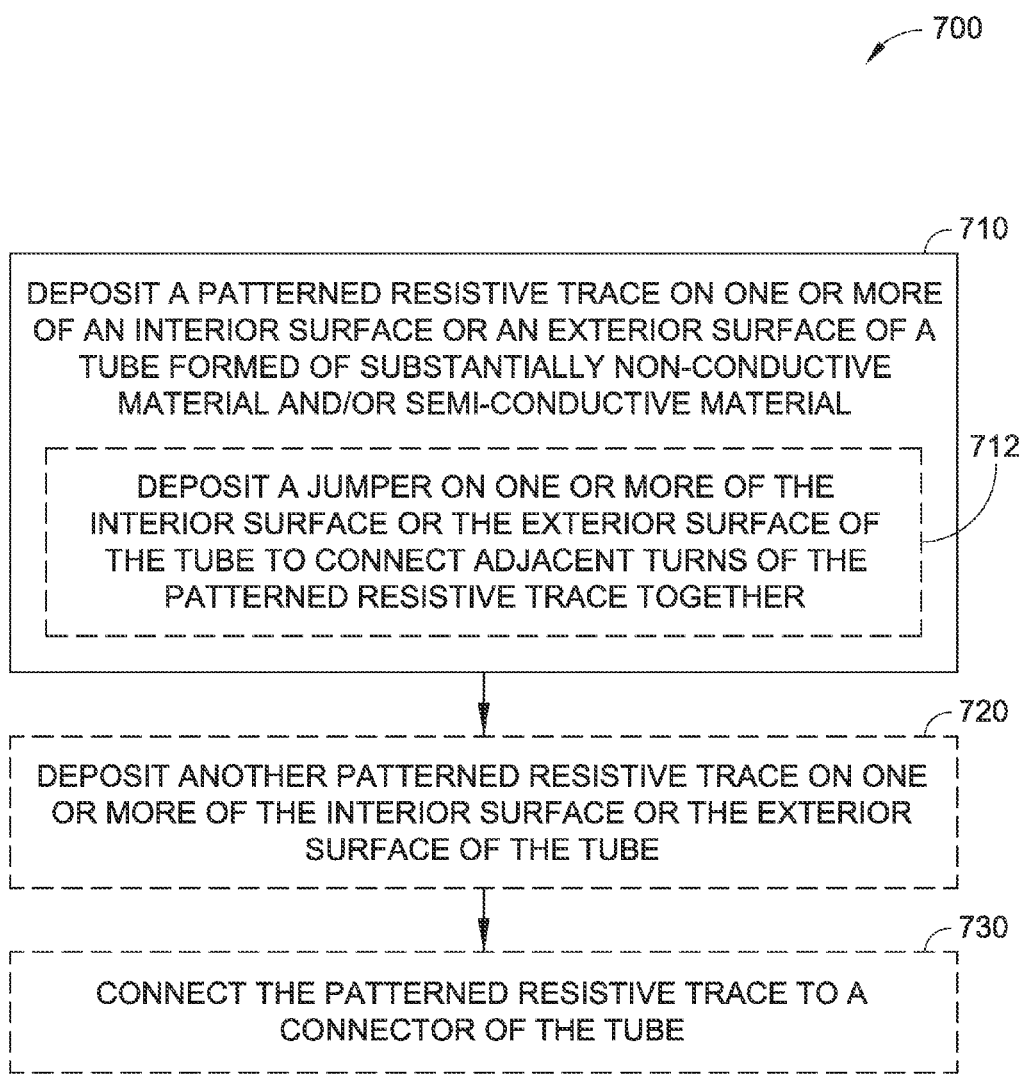
FIG. 7 is a flow diagram illustrating a method of manufacturing a charged material transportation chamber with a patterned resistive trace deposited on an interior surface and/or an exterior surface of the charged material transportation chamber in accordance with an example implementation of the present disclosure.

The following discussion describes example techniques for fabricating a charged material transportation chamber by depositing one or more patterned resistive traces on one or more of an interior surface or an exterior surface of a non-conductive or semi-conductive tube. FIG. 7 depicts a process 700, in an example implementation, for fabricating a charged material transportation chamber, such as the example drift tube 110 illustrated in FIGS. 1 through 6 and described above.

In the process 700 illustrated, a patterned resistive trace is deposited on one or more of an interior surface or an exterior surface of a tube formed of substantially non-conductive material and/or semi-conductive material (Block 710). For example, with reference to FIGS. 1 through 6, resistive trace 120 is deposited on interior surface 116 of tube 114 and/or exterior surface 118 of tube 114. The resistive trace 120 may be deposited (e.g., printed) on the interior surface 116 of the tube 114 and/or the exterior surface 118 of the tube 114 as described in United States Patent Publication Number 2008/0278278, filed Jul. 21, 2008, and titled "FINE LINE THICK FILM RESISTORS BY PHOTOLITHOGRAPHY;" U.S. Pat. No. 7,224,258, issued May 29, 2007, and titled, "Fine line thick film resistors by photolithography;" United States Patent Publication Number 2007/0262846, filed May 4, 2007, and titled, "FINE LINE THICK FILM RESISTORS BY PHOTOLITHOGRAPHY;" United States Patent Publication Number 2010/0209318, filed Apr. 28, 2010, and titled, "MICROFLUIDIC DEVICES FABRICATED BY DIRECT THICK FILM WRITING AND METHODS THEREOF;" U.S. Pat. No. 7,736,592, issued Jun. 15, 2010, and titled "Microfluidic devices fabricated by direct thick film writing and methods thereof;" United States Patent Publication Number 2011/0277803, filed Mar. 18, 2011, and titled, "THERMOCOUPLE DEVICE;" and/or U.S. Pat. No. 4,485,387, issued Nov. 27, 1984, and titled, "Inking system for producing circuit patterns," which are herein incorporated by reference in their entireties.

In some implementations, a jumper is deposited on one or more of the interior surface or the exterior surface of the tube to connect adjacent turns of the patterned resistive traces together (Block 712). For instance, with continuing reference to FIGS. 1 through 6, jumpers 128 can be used to connect adjacent turns of resistive trace 120 together. In some implementations, another patterned resistive trace is deposited on one or more of the interior surface or the exterior surface of the tube (Block 720). For example, with continuing reference to FIGS. 1 through 6, a second resistive trace 120 is deposited on exterior surface 118 of tube 114. As described, resistive traces 120 are configured to connect to a source of electrical energy to establish an electric field (e.g., a substantially uniform electric field, a shaped electric field, and so forth) within tube 114 when energized. In some implementations, the patterned resistive trace is connected to a connector of the tube, which is configured to connect the patterned resistive trace to the source of electrical energy (Block 730). For instance, with continuing reference to FIGS. 1 through 6, connector 130 can be formed to connect to resistive traces 120. As described, connector 130 can be formed as a conductive flange, a conductive cap, a conductive coating, and so forth. Connector 130 can then be connected to a source of electrical energy (e.g., a power supply) to energize a patterned resistive trace and establish an electric field.

Although the subject matter has been described in language specific to structural features and/or methodological acts, it is to be understood that the subject matter defined in the appended claims is not necessarily limited to the specific features or acts described. Although various configurations are discussed, the apparatus, systems, subsystems, components and so forth can be constructed in a variety of ways without departing from this disclosure. Rather, the specific features and acts are disclosed as example forms of implementing the claims.

What is claimed is:

1. A method of manufacturing a charged material transportation chamber for an ion detection assembly, the method comprising:

drawing, by an application tool, a patterned resistive trace comprising a fine line of resistive ink forming a plurality of adjacent segments on an interior surface of a longitudinal chamber formed of at least one of substantially non-conductive material or semi-conductive material, the interior surface of the longitudinal chamber defining a void cylindrical cavity forming a drift region, the patterned resistive trace configured to connect to a source of electrical energy, wherein the patterned resistive trace forms one or more electrodes configured to draw ions along the drift region, and the plurality of adjacent segments of the fine line of resistive ink extend from a first end of the longitudinal chamber to a second end of the longitudinal chamber, the second end being longitudinally opposite the first end;

longitudinally advancing the chamber with respect to the application tool;

rotating the chamber with respect to the application tool while drawing the patterned resistive trace;

connecting the plurality of adjacent segments of the patterned resistive trace to one another and to a connector of the chamber by drawing a longitudinal resistive trace on the interior surface of the longitudinal chamber from the first end of the longitudinal chamber to the second end of the longitudinal chamber that connects the plurality of adjacent segments of the patterned resistive trace and the connector so that the patterned resistive trace is physically continuous, the connector configured to connect the patterned resistive trace to the source of electrical energy;

placing an inlet assembly in fluid communication with the longitudinal chamber, the inlet assembly comprising an inlet for receiving a sample, a reaction region for ionizing the sample, and a gate for controlling entrance of the ionized sample to the longitudinal chamber; and placing a collector assembly in fluid communication with the longitudinal chamber, the collector assembly comprising a collector plate for collecting the ionized sample after the ionized sample passes through the longitudinal chamber.

2. The method as recited in claim 1, wherein the patterned resistive trace is configured to connect to the source of electrical energy to establish an electric field within the chamber when energized.

3. The method as recited in claim 1, wherein the patterned resistive trace is configured to connect to the source of electrical energy to heat the chamber when energized.

4. The method as recited in claim 1, wherein the patterned resistive trace comprises a turn deposited on at least one of the interior surface or the exterior surface of the chamber, the turn oriented at least substantially perpendicular to a longitudinal axis of the chamber.

5. The method as recited in claim 4, wherein the turn comprises a turn of at least two hundred and seventy degrees (270°).

6. The method as recited in claim 1, wherein the patterned resistive trace is configured as